(12) United States Patent
Li et al.

(10) Patent No.: US 11,046,687 B2
(45) Date of Patent: Jun. 29, 2021

(54) POLYCYCLIC AMIDE COMPOUND, PREPARATION PROCESS AND USE THEREOF

(71) Applicant: HEBEI GRANDIOS PHARMA CO., LTD., Hebei (CN)

(72) Inventors: Wei Li, Hebei (CN); Anya Yang, Hebei (CN); Shangjin Yang, Hebei (CN)

(73) Assignee: HEBEI GRANDIOS PHARMA CO., LTD.

( * ) Notice: Subject to any disclaimer, the term of this patent is extended or adjusted under 35 U.S.C. 154(b) by 52 days.

(21) Appl. No.: 16/566,397

(22) Filed: Sep. 10, 2019

(65) Prior Publication Data
US 2020/0079771 A1 Mar. 12, 2020

(30) Foreign Application Priority Data

Sep. 12, 2018 (CN) .......................... 201811059785.4

(51) Int. Cl.
*C07D 471/04* (2006.01)
*C07D 219/04* (2006.01)
*A61P 35/00* (2006.01)

(52) U.S. Cl.
CPC ............ *C07D 471/04* (2013.01); *A61P 35/00* (2018.01); *C07D 219/04* (2013.01)

(58) Field of Classification Search
CPC ...... C07D 471/04; C07D 219/04; A61P 35/00
See application file for complete search history.

(56) References Cited

FOREIGN PATENT DOCUMENTS

WO WO-03097642 A1 * 11/2003 ........... C07D 491/04

OTHER PUBLICATIONS

Deady etal Bioorganic and Medicinal Chemistry 2005, 13, 1341-1355. (Year: 2005).*
Eliel and Wilen, Stereochemistry of Organic Compounds, 1994, John Wiley and Sons, Inc. pp. 13, 481, 1208. (Year: 1994).*

* cited by examiner

*Primary Examiner* — John Mabry

(57) ABSTRACT

A novel polycyclic amide compound, preparation process and use thereof are provided. The compound has cytotoxic biological activity, particularly for the treatment and/or prevention of cell proliferative diseases such as cancer. This compound is a compound represented by Formula I or

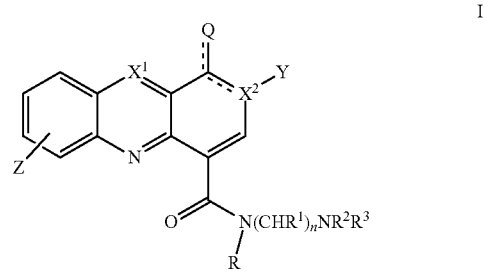

I a pharmaceutically acceptable salt, solvate, polymorph, enantiomer or racemic mixture, prodrug and N-oxide thereof, wherein, R, $R^1$-$R^3$ are independently selected from hydrogen, $C_{1-5}$ alkyl, or $C_{1-5}$ having a hydroxyl group or a halogen, and may be bonded to each other to form a ring, Z is an arbitrary substituent group, $X^1$ and $X^2$ may be carbon or nitrogen respectively, Q is oxygen or sulfur. Compared to the existing known polycyclic amide compounds, the novel polycyclic amide compound has more potent cytotoxicity and can be used for the treatment of diseases such as tumors, cancers, Alzheimer's disease, autoimmune diseases, cataracts, psychological disorders, depression and/or anxiety.

1 Claim, No Drawings

POLYCYCLIC AMIDE COMPOUND, PREPARATION PROCESS AND USE THEREOF

This application claims priority to Chinese Patent Application No. 201811059785.4 filed on Sep. 12, 2018, the disclosure of which is hereby incorporated in its entirety by reference.

FIELD

The present invention relates to a novel class of cytotoxic polycyclic amide compounds and preparation process thereof, and pharmaceutical compositions containing them and use thereof in therapy, particularly for the treatment and prevention of cell proliferative diseases such as cancer.

BACKGROUND

In recent years, DNA topoisomerase has become one of the hotspots in molecular biology research. Experiments have proven that DNA topoisomerase is directly related to cell proliferation, DNA replication, gene expression and anticancer drug studies. Many drugs, such as doxorubicin, Vp16, camptothecin, etc., exert cytotoxicity by affecting the activity of DNA topoisomerase. Topoisomerase is often used as a new target for screening anticancer drugs (Journal of Medicinal Chemistry, 2011, 5796-5810). Polycyclic aromatic chromophores with cationic side chains have successfully become DNA-embedded topoisomerase inhibitors. Two representative tricyclic compounds that exhibit cytotoxic effects and have the uses for anticancer drugs, for example, DACA (1), also known as XR5000, is acridine derivative (U.S. Pat. No. 4,590,277), and the compound (2) (J. Med. Chem. 2003, 46, 1049-1054) and phenazine-1-carboxamide (3) (EP0172744A2) are active against DNA-regulating enzymes topoisomerases I and I, and they have entered phase I clinical trials (J. Med. Chem. 1999, 42, 2383-2393, and Research & Reviews: Journal of Medicinal & Organic Chemistry, 2015, 67-76). The derivative (4) of benzo[b][1,6]naphthyridin-1(2H)-one (AU2003221640B2) also belongs to this class of compound and exhibits superior biological activity. The common feature of these types of compounds is the amide with a cationic side chain. In addition, the main structures of two tricyclic compounds can be connected through a flexible chain.

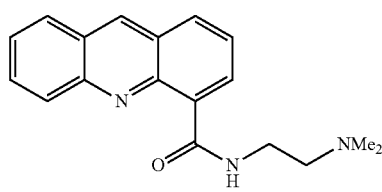

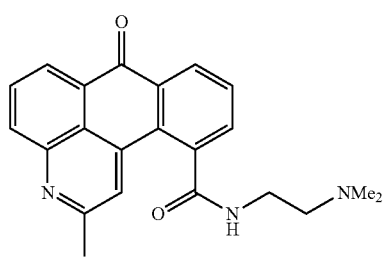

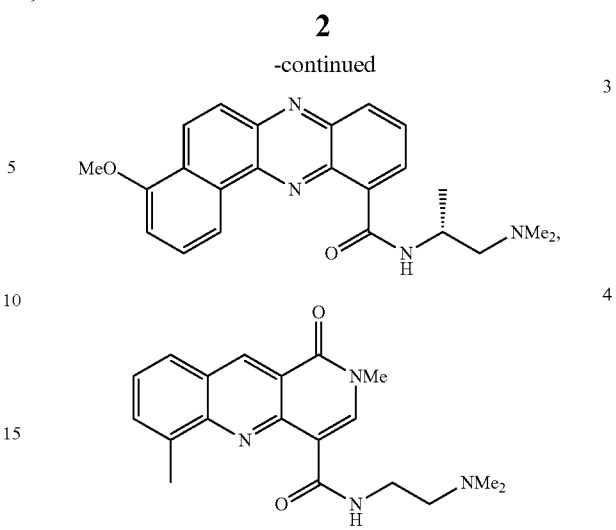

Although the tricyclic structures and the amide side chains of the three types of compounds have different structures, the original inventors believe that the relationship between the chemical structure and the potential efficacy of anticancer drugs is still unclear (AU2003221640B2). During the study of DACA (1), the amide group attached to the acridine ring has a formula of —CONH(CH$_2$)$_n$NR$^1$R$^2$, and R$^1$ and R$^2$ may be light alkanes having a hydroxyl group or an amino group, respectively. By detection, the compound has the highest activity when both R$^1$ and R$^2$ are methyl groups (U.S. Pat. No. 4,590,277) among a series of compounds. In view of this conclusion, the inventors mainly study the amide side chain —CONH (CH$_2$)$_2$NMe$_2$, and link it to many different tricyclic structures in the study of the derivatives of benzo[b][1,6] naphthyridine-1 (2H)-one. Many studies on the structure and activity of tricyclic compounds are also essentially limited to the standard side chain —CONH (CH$_2$)$_2$NMe$_2$ (Bioorganic & Medicinal Chemistry, 2006, 1160-1163), as N, N-dimethylethylenediamine is easily available and it is cheap. Although the inventors have defined that the substituents on the nitrogen of the amide side chain terminal may be different alkyl or substituted alkyl groups, respectively in the claims of the above several patents, this type of compounds have never appeared, as far as we know. For benzo[b][1,6]naphthyridin-1(2H) one, although inventors have studied other amide side chains, they are only limited to —CONHCHMeCH$_2$NMe$_2$ and —CONHCHMeCONMe$_2$(AU2003221640B2), which are only slightly different from the former in terms of the structure; while such a slight difference makes the activity of the compounds to reduce greatly as much as four orders of magnitude (17,000 vs. 2). The inventors have not conducted in-depth study on other amide side chains.

SUMMARY

According to the background art, not only the tricyclic structure of the compound affects the biological activity, but also the amide side chain plays an extremely important role. Therefore, based on the potential uses of these compounds, extending the structural types of these amide side chains is of great significance to the drug development.

When 5-methylacridine-4-carboxylic acid reacts with 8-aminoquinoline to form an amide, it is surprisingly found through biological activity detection that its activity is nearly four times larger than that already reported by the patent. This further confirms our hypothesis that the biological activity of the above three types of compounds can be greatly improved by changing amide side chains.

In order to synthesize compounds with different groups on the nitrogen terminal of the amide side chain, we design the synthetic route as follows:

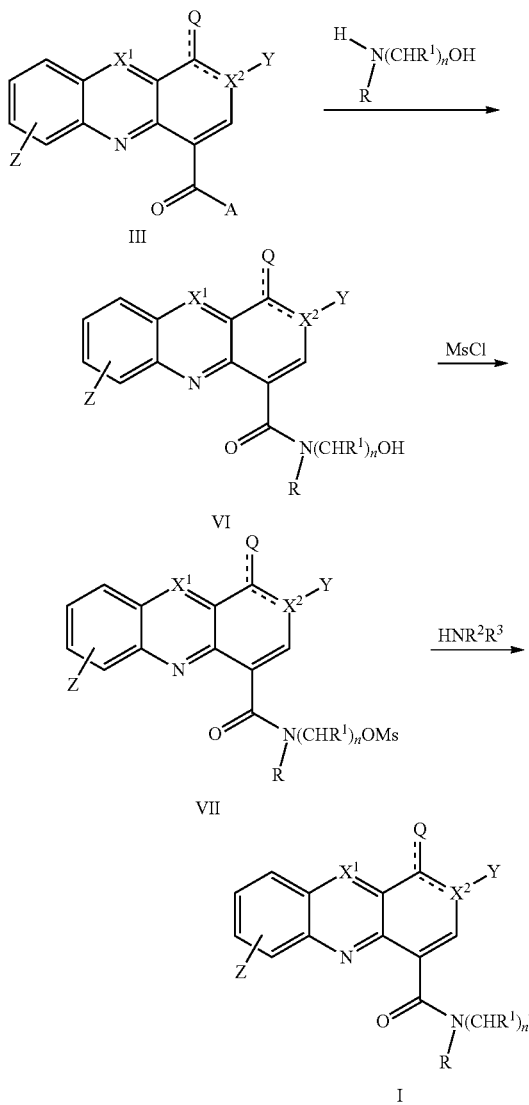

The definitions herein are described in the part of the Description of the invention.

The tricyclic carboxylic acids listed herein can be synthesized with reference to the literatures. The resulting tricyclic carboxylic acid firstly reacts with hydroxylamine to form an alkyl amide with a terminal hydroxyl group on the nitrogen, and then the terminal hydroxyl group is sulfonylated, and finally reacts with different primary and secondary amines to give the target compound. As can be seen from the above figure, this synthesis route allows to link different substituents to the terminal nitrogen easily.

It is specifically noted herein that although many prior art and patents are listed herein, the synthetic methods exhibited by the present invention as well as the synthesis and assay of a series of tricyclic amide compounds are more diverse and different from those previously reported. Representative examples of these compounds can be used as cytotoxic agents and anticancer drugs.

The tricyclic amide compound of the present invention has the following structural formula.

According to a first aspect, the present invention provides a compound of chemical structural formula I

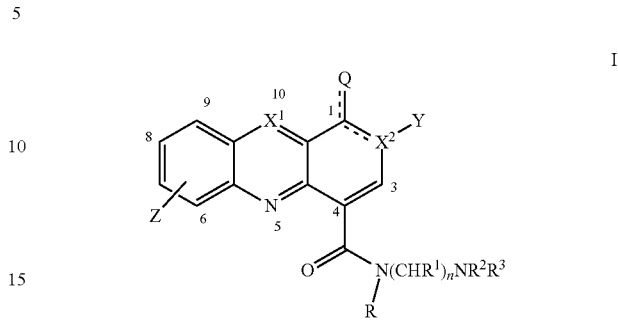

wherein the position number is as shown in the above chemical structure,
wherein:
$X^1$ are $X^2$ may be —CH= or —N= respectively or simultaneously;
Q is O or S;
R and $R^1$-$R^3$ are independently H or optionally substituted $C_1$ alkyl or R and $R^1$-$R^3$ together with the bonded nitrogen atoms to form an optionally substituted saturated or unsaturated heterocyclic group;
n is an integer from 0 to 6;
However, when $X^2$ is carbon, n $R^1$ is not H simultaneously; and when $X^2$ is nitrogen and n=2, $R^2$ and $R^3$ are not methyl(Me) simultaneously;
Z is H, halogen, OH, $CO_2H$, $CO_2R^4$, $SO_2R^4$, $NR^4R^5$, nitro, cyano, $C_{1-6}$ alkyl, $C_{1-6}$ haloalkyl, $C_{1-6}$ alkoxy, $C_{1-6}$ haloalkoxy, $C_{1-6}$ aminoalkyl, $C_{1-6}$ aminoalkoxy, or aza functional group-substituted cyclic CH functional group, or bridged carbon or carbon/nitrogen skeleton at positions 6-7, 7-8 or 8-9, to form additional condensed 5- to 6-membered carbocyclic ring or heterocyclic ring;
R and $R^1$-$R^3$ are independently H or optionally substituted $C_{1-4}$ alkyl or R and $R^1$-$R^3$ together with the bonded nitrogen atoms to form an optionally substituted saturated or unsaturated heterocyclic group, n is an integral from 0 to 6.
Y is H, $C_{1-6}$ alkyl, having an active group $C_1$-$C_6$ alkyl or $(CH_2)_m$—$X^2$—$(CH_2)_p$U defined same as Z, wherein $X^2$ is $CH_2$, C=O, CH=CH, O, S, NR;
m and p are integers from 0 to 6;
U is H, $CF_3$, halogen, $NR^4R^5$, $^+NRR^4R^5$, cyano, C(=O) $NR^4R^5$ $OR^4$, or $CO_2R^4$;
The optional substituents for $R^4$ and $R^5$ are the same as those defined for R and $R^1$-$R^3$; or a pharmaceutically acceptable salt, an N-oxide, a hydrate, a solvate, a pharmaceutically acceptable derivative, a prodrug, a tautomer and/or an isomer of the compound.

Preferably, in the formula (I), Z is 6-H, $X^1$ is —CH=, Y is H, Q is H, $R^{1a}$ and $R^{1b}$ are not H simultaneously, as shown in the Formula Ia:

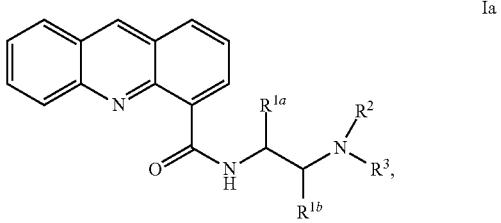

Representative compounds of the present invention can be illustrated by the compounds listed in Table 1 below, but the present invention is not limited to these compounds.

TABLE 1

| Compound No. | $R^{1a}$ | $R^{1b}$ | $R^2$ | $R^3$ |
|---|---|---|---|---|
| 5 | H | Me | Me | H |
| 6 | H | Me | Et | H |
| 7 | H | Me | Et | Me |
| 8 | H | Me | Et | Et |
| 9 | H | Me | i-Pr | H |
| 10 | H | Me | i-Pr | Me |
| 11 | H | Me | i-Pr | Et |
| 12 | H | Me | c-Pr | H |
| 13 | H | Me | c-Pr | Me |
| 14 | H | Me | —CH$_2$CH$_2$OH | H |
| 15 | H | Me | —CH$_2$CH$_2$OH | Me |
| 16 | H | Me | i-Bu | H |
| 17 | H | Me | i-Bu | Me |
| 18 | H | Me | —(CH$_2$)$_4$— | |
| 19 | H | Me | —(CH$_2$)$_5$— | |
| 20 | H | Me | Me | Me |
| 21 | Me | H | Me | H |
| 22 | Me | H | Et | H |
| 23 | Me | H | Et | Me |
| 24 | Me | H | Et | Et |
| 25 | Me | H | i-Pr | H |
| 26 | Me | H | i-Pr | Me |
| 27 | Me | H | i-Pr | Et |
| 28 | Me | H | c-Pr | H |
| 29 | Me | H | c-Pr | Me |
| 30 | Me | H | —CH$_2$CH$_2$OH | H |
| 31 | Me | H | —CH$_2$CH$_2$OH | Me |
| 32 | Me | H | i-Bu | H |
| 33 | Me | H | i-Bu | Me |
| 34 | Me | H | —(CH$_2$)$_4$— | |
| 35 | Me | H | —(CH$_2$)$_5$— | |
| 36 | Me | H | —(CH$_2$)$_2$—O—(CH$_2$)$_2$— | |
| 37 | Me | H | Me | Me |
| 38 | —(CH$_2$)$_3$— | | Me | Me |
| 39 | —(CH$_2$)$_4$— | | Me | Me |
| 40 | =CH—CH=CH—CH= | | Me | Me |
| 41 | H | | —(CH$_2$)$_3$— | Me |
| 42 | H | | —(CH$_2$)$_4$— | Me |
| 43 | H | | —(CH$_2$)$_5$— | Me |

44

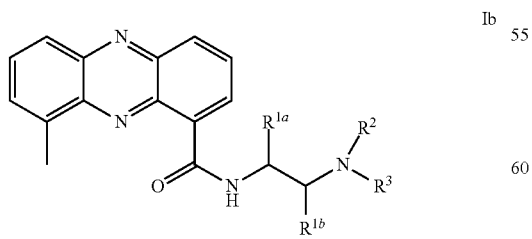

Preferably, in the formula (I), Z is 6-Me, $X^1$ is —N=, $X^2$=C=, Y is H, Q is H, $R^{1a}$ and $R^{1b}$ are not H simultaneously, as shown in the Formula Ib:

Ib

Representative compounds of the present invention can be illustrated by the compounds listed in Table 2 below, but the present invention is not limited to these compounds.

TABLE 2

| Compound No. | $R^{1a}$ | $R^{1b}$ | $R^2$ | $R^3$ |
|---|---|---|---|---|
| 45 | H | Me | Me | H |
| 46 | H | Me | Et | H |
| 47 | H | Me | Et | Me |
| 48 | H | Me | Et | Et |
| 49 | H | Me | i-Pr | H |
| 50 | H | Me | i-Pr | Me |
| 51 | H | Me | i-Pr | Et |
| 52 | H | Me | c-Pr | H |
| 53 | H | Me | c-Pr | Me |
| 54 | H | Me | —CH$_2$CH$_2$OH | H |
| 55 | H | Me | —CH$_2$CH$_2$OH | Me |
| 56 | H | Me | i-Bu | H |
| 57 | H | Me | i-Bu | Me |
| 58 | H | Me | —(CH$_2$)$_4$— | |
| 59 | H | Me | —(CH$_2$)$_5$— | |
| 60 | H | Me | Me | Me |
| 61 | Me | H | Me | H |
| 62 | Me | H | Et | H |
| 63 | Me | H | Et | Me |
| 64 | Me | H | Et | Et |
| 65 | Me | H | i-Pr | H |
| 66 | Me | H | i-Pr | Me |
| 67 | Me | H | i-Pr | Et |
| 68 | Me | H | c-Pr | H |
| 69 | Me | H | c-Pr | Me |
| 70 | Me | H | —CH$_2$CH$_2$OH | H |
| 71 | Me | H | —CH$_2$CH$_2$OH | Me |
| 72 | Me | H | i-Bu | H |
| 73 | Me | H | i-Bu | Me |
| 74 | Me | H | —(CH$_2$)$_4$— | |
| 75 | Me | H | —(CH$_2$)$_5$— | |
| 76 | Me | H | —(CH$_2$)$_2$—O—(CH$_2$)$_2$— | |
| 77 | Me | H | Me | Me |
| 78 | —(CH$_2$)$_3$— | | Me | Me |
| 79 | —(CH$_2$)$_4$— | | Me | Me |
| 80 | =CH—CH=CH—CH= | | Me | Me |
| 81 | H | | —(CH$_2$)$_3$— | Me |
| 82 | H | | —(CH$_2$)$_4$— | Me |
| 83 | H | | —(CH$_2$)$_5$— | Me |

84 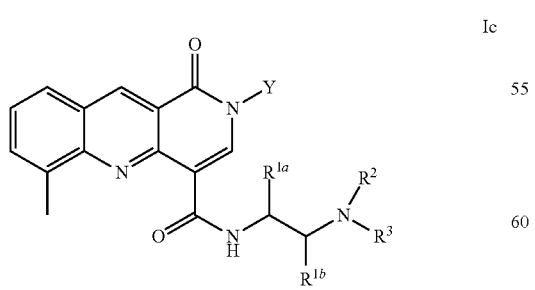

Preferably, in the formula (I), Z is 6-Me, $X^1$ is —CH=, $X^2$—N—, and Q is oxygen, but excluding the following three amide side chains that have been disclosed: —CONHCH$_2$CH$_2$N(CH$_3$)$_2$, —CONHCHMeCH$_2$N(CH$_3$)$_2$, —CONHCHMeCON(CH$_3$)$_2$. As shown in the formula Ic:

Ic

Representative compounds of the present invention can be illustrated by the compounds listed in Table 3 below, but the present invention is not limited to these compounds.

TABLE 3

| Compound No. | Y | R¹ᵃ | R¹ᵇ | R² | R³ |
|---|---|---|---|---|---|
| 85 | C₆H₄F-4 | H | H | Me | H |
| 86 | C₆H₄F-4 | H | H | Et | Me |
| 87 | Me | H | H | Et | H |
| 88 | Me | H | H | Et | Me |
| 89 | Me | H | H | Et | Et |
| 90 | Et | H | H | Et | Me |
| 91 | C₆H₄F-4 | H | H | Et | Et |
| 92 | Me | H | H | i-Pr | H |
| 93 | Me | H | H | i-Pr | Me |
| 94 | C₆H₄F-4 | H | H | i-Pr | Et |
| 95 | C₆H₄F-4 | H | H | c-Pr | H |
| 96 | Me | H | H | c-Pr | Me |
| 97 | C₆H₄F-4 | H | H | —CH₂CH₂OH | H |
| 98 | Me | H | H | —CH₂CH₂OH | Me |
| 99 | C₆H₄F-4 | H | H | i-Bu | H |
| 100 | Me | H | H | i-Bu | Me |
| 101 | C₆H₄F-4 | H | H | —(CH₂)₄— | |
| 102 | Me | H | H | —(CH₂)₅— | |
| 103 | Me | H | H | —(CH₂)₂O(CH₂)₂— | |
| 104 | Et | H | Me | Me | Me |
| 105 | Me | —(CH₂)₃— | | Me | Me |
| 106 | Me | —(CH₂)₄— | | Me | Me |
| 107 | C₆H₄F-4 | =CH—CH=CH—CH= | | Me | Me |
| 108 | C₆H₄F-4 | H | —(CH₂)₃— | | Me |
| 109 | Et | H | Me | Me | H |
| 110 | Et | H | Me | Et | H |
| 111 | C₆H₄F-4 | H | Me | Et | Me |
| 112 | C₆H₄F-4 | H | Me | Et | Et |
| 113 | Me | H | Me | i-Pr | H |
| 114 | Me | H | Me | i-Pr | Me |
| 115 | Et | H | Me | i-Pr | Et |
| 116 | C₆H₄F-4 | H | Me | c-Pr | H |
| 117 | Me | H | Me | c-Pr | Me |
| 118 | Et | H | Me | —CH₂CH₂OH | H |
| 119 | Me | H | Me | —CH₂CH₂OH | Me |
| 120 | C₆H₄F-4 | H | Me | i-Bu | H |
| 121 | C₆H₄F-4 | H | Me | i-Bu | Me |
| 122 | Et | H | Me | —(CH₂)₄— | |
| 123 | Me | H | Me | —(CH₂)₅— | |
| 124 | C₆H₄F-4 | H | Me | Me | Me |
| 125 | Et | Me | H | Me | H |
| 126 | C₆H₄F-4 | Me | H | Et | H |
| 127 | Me | Me | H | Et | Me |
| 128 | C₆H₄F-4 | Me | H | Et | Et |
| 129 | Me | Me | H | i-Pr | H |
| 130 | Me | Me | H | i-Pr | Me |
| 131 | Et | Me | H | i-Pr | Et |
| 132 | Me | Me | H | c-Pr | H |
| 133 | C₆H₄F-4 | Me | H | c-Pr | Me |
| 134 | Et | Me | H | —CH₂CH₂OH | H |
| 135 | Me | Me | H | —CH₂CH₂OH | Me |
| 136 | C₆H₄F-4 | Me | H | i-Bu | H |
| 137 | Et | Me | H | i-Bu | Me |
| 138 | C₆H₄F-4 | Me | H | —(CH₂)₄— | |
| 139 | C₆H₄F-4 | Me | H | —(CH₂)₅— | |
| 140 | C₆H₄F-4 | Me | H | —(CH₂)₆— | |
| 141 | Me | 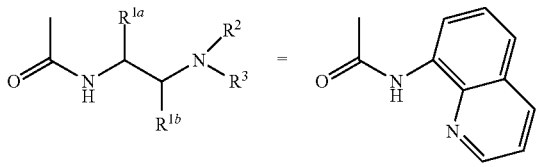 | | | |

The invention further provides a compound of formula II, a derivative of benzo[b][1,6]naphthyridin-1(2H)-one, or a pharmaceutically acceptable salt thereof or an N-oxide thereof:

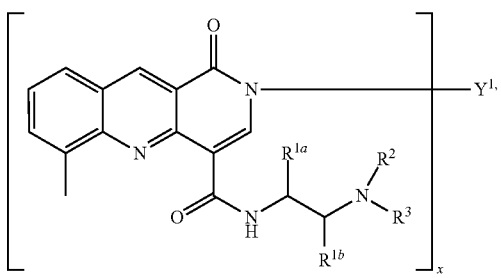

II $R^1$-$R^3$ are independently H, or optionally substituted $C_{1-4}$ alkyl groups, or $R^1$-$R^3$ form saturated or unsaturated cyclic group with each other, or form optionally substituted or unsaturated heterocyclic group together with the bonded nitrogen or oxygen atom, but excluding the already disclosed amide side chain: i.e., when $R^2$, $R^3$ are both methyl, $R^{1a}$ and $R^{1b}$ are H, and when $R^2$, $R^3$, $R^{1a}$ all are methyl, $R^{1b}$ is H or carbonyl, represented by a chemical formula: —CONHCH$_2$CH$_2$N(CH$_3$)$_2$, —CONHCHMeCH$_2$N(CH$_3$)$_2$, —CONHCHMeCON(CH$_3$)$_2$;

$Y^1$ is a linking group —(CH$_2$)$_m$—X$^2$—(CH$_2$)$_p$U of valence x, wherein $X^2$ is CH$_2$, C=O, CH=CH, O, S, NR;

m and p are integers from 0 to 6;

U is H, CF$_3$, halogen, NR$^4$R$^5$, $^+$NRR$^4$R$^5$, cyano, C(=O)R$^4$R$^5$ OR$^4$, or CO$_2$R$^4$;

the optional substituents for $R^4$ and $R^5$ are the same as those for R and $R^1$-$R^3$;

or a pharmaceutically acceptable salt, an N-oxide, a hydrate, a solvate, a pharmaceutically acceptable derivative, a prodrug, a tautomer and/or an isomer of the compound.

x is preferably 2.

Most preferably, $Y^1$ is selected from the following:
—(CH$_2$)$_2$NH(CH$_2$)$_2$—
—(CH$_2$)$_3$—NMe—(CH$_2$)$_3$—
—(CH$_2$)$_2$NH(CH$_2$)$_2$NH(CH$_2$)$_2$—
—(CH$_2$)$_2$NH(CH$_2$)$_3$NH(CH$_2$)$_2$—
—(CH$_2$)$_2$NMe(CH$_2$)$_2$NMe(CH$_2$)$_2$—
—(CH$_2$)$_2$NMe(CH$_2$)$_3$NMe(CH$_2$)$_2$—
—N, N'-bis(ethylene) piperazine-,
—N, N'-bis(propenyl)piperazine-, —(CH$_2$)$_s$NH(CH$_2$)$_t$—
—(CH$_2$)$_s$NAlkyl(CH$_2$)$_t$—
—(CH$_2$)$_s$NH(CH$_2$)$_t$NH(CH$_2$)$_u$—,
—(CH$_2$)$_s$NAlkyl(CH$_2$)$_t$NAlkyl(CH$_2$)$_u$—, where s, t and u are integers from 2 to 6.

But the following three amide side chains that have been disclosed are excluded: —CONHCH$_2$CH$_2$N(CH$_3$)$_2$, —CONHCHMeCH$_2$N(CH$_3$)$_2$, —CONHCHMeCON(CH$_3$)$_2$, Representative compounds of the present invention can be illustrated by the compounds listed in Table 4 below, but the present invention is not limited to these compounds.

TABLE 4

| Compound No. | $Y^1$ | $R^{1a}$ | $R^{1b}$ | $R^2$ | $R^3$ |
|---|---|---|---|---|---|
| 142 | —(CH$_2$)$_2$NMe(CH$_2$)$_3$NMe(CH$_2$)$_2$— | H | H | Et | Me |
| 143 | —(CH$_2$)$_2$NMe(CH$_2$)$_3$NMe(CH$_2$)$_2$— | H | H | i-Pr | Me |
| 144 | —(CH$_2$)$_2$NMe(CH$_2$)$_3$NMe(CH$_2$)$_2$— | H | H | Et | Et |
| 145 | —(CH$_2$)$_2$NMe(CH$_2$)$_3$NMe(CH$_2$)$_2$— | H | H | —(CH$_2$)$_2$OH | H |
| 146 | —(CH$_2$)$_2$NMe(CH$_2$)$_3$NMe(CH$_2$)$_2$— | H | H | —(CH$_2$)$_4$— | |
| 147 | —(CH$_2$)$_2$NMe(CH$_2$)$_3$NMe(CH$_2$)$_2$— | Me | H | Et | Me |
| 148 | —(CH$_2$)$_2$NMe(CH$_2$)$_3$NMe(CH$_2$)$_2$— | Me | H | i-Pr | Me |
| 149 | —(CH$_2$)$_2$NMe(CH$_2$)$_3$NMe(CH$_2$)$_2$— | Me | H | Et | Et |
| 150 | —(CH$_2$)$_2$NMe(CH$_2$)$_3$NMe(CH$_2$)$_2$— | Me | H | —(CH$_2$)$_2$OH | H |
| 151 | —(CH$_2$)$_2$NMe(CH$_2$)$_3$NMe(CH$_2$)$_2$— | Me | H | —(CH$_2$)$_4$— | |
| 152 | —(CH$_2$)$_2$NMe(CH$_2$)$_3$NMe(CH$_2$)$_2$— | H | Me | Et | Me |
| 153 | —(CH$_2$)$_2$NMe(CH$_2$)$_3$NMe(CH$_2$)$_2$— | H | Me | i-Pr | Me |
| 154 | —(CH$_2$)$_2$NMe(CH$_2$)$_3$NMe(CH$_2$)$_2$— | H | Me | Et | Et |
| 155 | —(CH$_2$)$_2$NMe(CH$_2$)$_3$NMe(CH$_2$)$_2$— | H | Me | —(CH$_2$)$_2$OH | H |
| 156 | —(CH$_2$)$_2$NMe(CH$_2$)$_3$NMe(CH$_2$)$_2$— | H | Me | —(CH$_2$)$_4$— | |

The compound of the formula (I) and pharmaceutically acceptable salts thereof, and the N-oxide thereof are prepared by the following two methods. The specific steps of the first method are as follows:

Step 1: Add tricyclic acid of formula (III) (1 g) and DMF (10 ml), 3 molar equivalents of amine of formula (IV) and 1.2 moles of O-benzotriazole-tetramethylurea hexafluorophosphate (HBTU) into a dry round-bottom flask.

Step 2: Carry out magnetic stirring at room temperature for 10-20 minutes, then slowly add N, N-diisopropylethylamine (2.0 moles), and then heat the reaction solution to 50° C. for 12 hours, and track the extent of reaction by TLC.

Step 3: Cool after the reaction is completed, pour the reaction solution into ice water, extracted with ethyl acetate. Combine the extracting solution, evaporate the solvent under reduced pressure after drying, and carry out column chromatography separation and purification of the residue using ethyl acetate: petroleum ether at a ratio of 1:1-1:9 as eluent, and recrystallize the eluent in a mixed solvent of ethyl acetate and petroleum ether after concentration.

The structural formulas of formula (III) and formula (IV) are as follows:

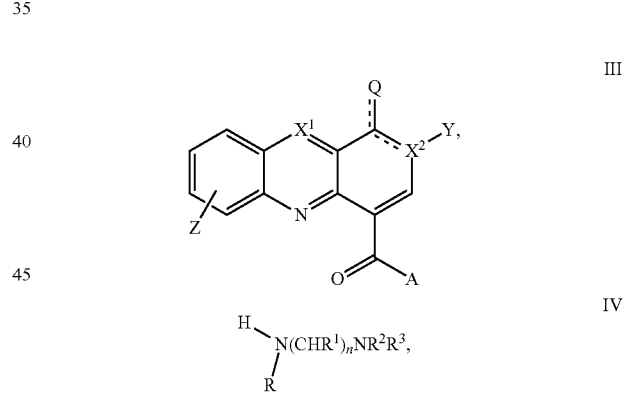

The specific steps of the second method are as follows:

Step 1: Add tricyclic acid of formula (III) (1 g) and DMF (10 ml), 3 molar equivalents of alkanolamine of formula (V) and 1.2 moles of O-benzotriazole-tetramethylurea hexafluorophosphate (HBTU) into a dry round-bottom flask.

Step 2: Carry out magnetic stirring at room temperature for 10-20 minutes, then slowly add N, N-diisopropylethylamine (2.0 moles), and then heat the reaction solution to 50° C. for 12 hours, and track the extent of reaction by TLC.

Step 3: Cool after the reaction is completed, pour the reaction solution into ice water, extracted with ethyl acetate. Combine the extracting solution, evaporate the solvent under reduced pressure after drying, and carry out column chromatography separation and purification of the residue using ethyl acetate: petroleum ether at a ratio of 1:1-1:9 as eluent, and recrystallize the eluent in a mixed solvent of ethyl acetate and petroleum ether after concentration, to give the alcohol of the formula (VI).

The structural formulas of formula (V) and formula (VI) are as follows:

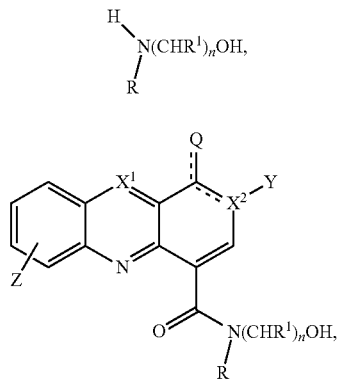

Step 4: Add an alcohol of the formula (VI) (1 g) and dichloromethane (10 ml) and 1.5 equivalents of triethylamine into a dry round-bottom flask.

Step 5: Carry out magnetic stirring under ice water condition, slowly add 1.3 molar equivalents of methylsulfonyl chloride after 10-20 minutes to react 1 hour, and track the extent of reaction by TLC.

Step 6: After the reaction is completed, add 20 ml of aqueous solution of sodium hydrogencarbonate, and after stirring for 10 minutes, the layers are separated, and the aqueous layer is extracted with dichloromethane, and the extracting solutions are combined and washed with diluted hydrochloric acid, aqueous solution of sodium hydrogencarbonate, and aqueous solution of saturated sodium chloride respectively. After drying, the solvent is evaporated under reduced pressure to give a compound of formula (VII).

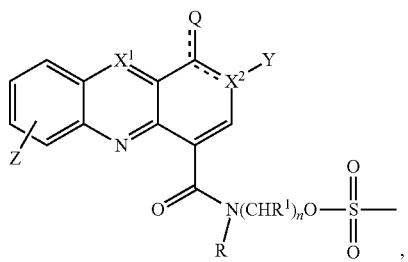

Step 7: Add the compound of the formula (VII) (0.1 g), DMSO (2 ml), and 3 molar equivalents of the compound of formula (VIII) into a dry round bottom flask. Mix them at room temperature overnight, add 20 ml of water, after stirring for 10 minutes, extract with dichloromethane, then combine the extracting solutions, and wash with diluted hydrochloric acid, aqueous solution of sodium hydrogencarbonate, and aqueous solution of saturated sodium chloride respectively. After drying, the solvent is evaporated under reduced pressure to give the compounds of the formulas (I) and (II).

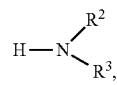

In the present invention, a pharmaceutical or veterinary composition comprising a compound of formula I, II as defined above, and a pharmaceutically or veterinarily acceptable carrier is provided.

Use of the present invention in the medicines for the treatment and prevention of cell proliferative diseases comprises administering a therapeutically effective dose of a compound of formula I to a subject in need thereof.

The invention further provides the use of a compound of formula I for preparing a medicine for the treatment and prevention of cell proliferative diseases.

The invention further provides a compound of formula I for use as a medicine for the treatment and prevention of cell proliferative diseases.

The invention still further provides the use of a compound of formula I as a cytotoxic, antitumor, antitumor and/or anticancer agent.

The present invention has the following advantages: the simple and easily available tricyclic formic acid and various amines are used as raw materials and HBTU as a shrinking agent. The synthetic route has the advantages of easy availability of raw materials, simple operation, mild reaction conditions, short reaction time, solvent saving and pollution reduction, etc., so it is convenient for industrial production.

DETAILED DESCRIPTION

The word "comprising/including" in the description means "including but not limited to". The singular forms "a", "an", "the" used herein include multiple aspects, unless explicitly specified otherwise. Thus, when referring to "the compound of formula I or II", it includes a single compound, and may also mean two or more compounds, and so forth.

The term "$C_{1-4}$ alkyl" or "$C_{1-6}$ alkyl" may be used alone or in a compound word, for example, "optionally substituted $C_{1-4}$ or $C_{1-6}$ alkyl", "$C_{1-6}$ haloalkyl" or "$C_{1-6}$ aminoalkyl". The "alkyl" means a straight-chain, branched or cyclic hydrocarbon group having 1 to 6 carbon atoms. Examples of such alkyl groups are methyl, ethyl, propyl, isopropyl, butyl, isobutyl, sec-butyl, tert-butyl, pentyl, neopentyl, hexyl, cyclopropyl, cyclobutyl, cyclopentyl or cyclohexyl.

The term "$C_{1-6}$ alkoxy" as used alone or in a compound word, such as "$C_{1-6}$ haloalkoxy" or "$C_{1-6}$ aminoalkoxy", refers to a straight or branched oxygen-containing group, each of which having a alkyl moiety having from 1 to about 6 carbon atoms. Examples of alkoxy groups include methoxy, ethoxy, propoxy, butoxy and tert-butoxy.

The term "linking group" is used herein in its broadest sense, and it refers to any organic group that connects adjacent units of a compound together and may be symmetrical or asymmetrical. Although the linking group is preferably a nitrogen-containing linking group, it is understood that it may be O; S; an optionally substituted $C_{1-20}$ alkylene, alkenylene or alkynylene chain, which may optionally be interspersed with one or more optionally substituted aryl or optionally substituted heterocyclic groups or one or more O, S or N atoms; or an optionally substituted saturated or unsaturated aryl or heterocyclic group.

The process for preparing the compounds of formulas I, II comprises reacting directly with the amine in the presence of a dehydrating agent, and may also comprises an intermediate step, for example, converting the compound of formula III to the imidazolide, reacting with the appropriate amine to give formula I or II. Alternatively, converting carboxylic acid of formula III to an acyl halide and then reacting with an amine to give the target amide of formula I, II. The reagent in this second route is preferably thionyl chloride. It will be clearly understood from the above description that in the presence of double compounds, two units of carboxylic acid react with appropriate diamine to form the target diamide.

The salts of the compounds of formula I or II are preferably pharmaceutically acceptable, but it should be understood that non-pharmaceutically acceptable salts are also within the scope of the invention, as they may be used for preparing pharmaceutically acceptable intermediates. Examples of pharmaceutically acceptable salts include pharmaceutically acceptable cationic salts such as sodium, potassium, lithium, calcium, magnesium, ammonium and alkylammonium; acid addition salts of pharmaceutically acceptable inorganic acids, such as hydrochloric acid, orthophosphoric acid, sulfuric acid, phosphoric acid, nitric acid, carbonic acid, boric acid, sulfamic acid and hydrobromic acid; or pharmaceutically acceptable salts of an organic acid, such as acetic acid, chloroacetic acid, dichloroacetic acid, propionic acid, butyric acid, tartaric acid, maleic acid, hydroxymaleic acid, fumaric acid, citric acid, lactic acid, mucilage, gluconic acid, benzoic acid, succinic acid, oxalic acid, phenylacetic acid, methanesulfonic acid, trihalomethanesulfonic acid, toluenesulfonic acid, benzene sulfonic acid, salicylic acid, sulfamic acid, aspartic acid, glutamic acid, ethylenediaminetetraacetic acid, stearic acid, palmitic acid, oleic acid, lauric acid, pantothenic acid, tannic acid, ascorbic acid and valeric acid.

In addition, some of the compounds of the present invention may form solvates with water or common organic solvents. These solvates are also included within the scope of the invention. "Pharmaceutically acceptable derivative" means any pharmaceutically acceptable salt, hydrate, ester, amide, active metabolite, analog, residue or any other compound which is not biologically or otherwise undesirable and induces the desired pharmacological or physiological effects.

The term "prodrug" is used herein in its broadest sense, including those compounds that are converted in vivo into compounds of formula I or II.

The term "tautomer" is used herein in its broadest sense, including compounds of formula I or II that are present in an equilibrium state between two isomeric forms. These compounds may differ in the bonds that link two atoms or groups or differ in the position of these atoms or groups.

The term "isomer" is used herein in its broadest sense, including structural, geometric and stereoisomers. Since the compound of formula I or II may have one or more chiral centers, it can exist as an enantiomer.

The compositions of the present invention comprise at least one compound of Formulas I, II and one or more pharmaceutically acceptable carriers and optionally other therapeutic agents. Each carrier, diluent, adjuvant or excipient must be pharmaceutically "acceptable" in terms of compatibility with other ingredients of the composition and no harm to subjects. Compositions include those suitable for oral, rectal, nasal, topical (including buccal and sublingual), vaginal or parenteral (including subcutaneous, intramuscular, intravenous and intradermal) administration. The compositions may be present in a single dosage form conveniently and may be prepared by methods well known in the art. These methods include the steps of binding the active ingredients with carriers which constitute one or more auxiliary ingredients. In general, the compositions are prepared by uniformly and tightly binding the active ingredients with the liquid carrier, diluent, adjuvant or excipient or finely-divided solid carrier or both, and forming the product if necessary.

"Cell proliferative disease" means that one or more cells exhibit abnormal growth, and usually the abnormal growth causes a tumor or a cancer.

The cell proliferative diseases include, for example, breast cancer, lung cancer, prostate cancer, kidney cancer, skin cancer, neurocarcinoma, ovarian cancer, uterine cancer, liver cancer, pancreatic cancer, epithelial cancer, gastric cancer, intestinal cancer, exocrine cancer, endocrine cancer, and diseases of lymphatic vessel, hematopoietic system or head and neck tissues.

Generally, neoplastic diseases are in a condition in which abnormal proliferation of cells causes a large amount of tissues to be called a tumor. Tumors are characterized by varying degrees of abnormalities in structure and behavior. Some tumors are benign, while some tumors are malignant. Effective treatment of neoplastic disease is considered a valuable contribution to the search for cancer prevention or treatment procedures. The compounds of the present invention are preferably used for the treatment of leukemia, lymphoma, multiple myeloma, sarcoma and brain tumor, as well as lung cancer, breast cancer, ovarian cancer, testicular cancer and colon cancer.

Other drugs may include one or more other anti-tumor agents, including but not limited to anti-mitotic agents such as paclitaxel, antimetabolites such as 5-fluorouracil, hormone modulators such as tamoxifen, DNA reagents such as cisplatin, or biological agents, such as interleukin-2 (IL-2) or antibodies.

The second DNA-binding anti-cancer therapeutic agent can be used in combination with the compound of Formula I or II to reduce toxic side effects or side effects to a recipient of one or both of the compounds of Formula I or II or other anticancer agents.

It is expected that the compounds of the present invention may also be administered in the form of a tumor-activating prodrug, wherein the active agent is linked to a "trigger" domain; for example, these compounds may be designed to be activated by local hypoxia within the tumor mass.

The compounds of the present invention may also be used in combination with agents which alleviate the side effects caused by medications such as granulocyte-macrophage colony stimulating factor (GM-CSF) or antiemetic.

As used herein, a "pharmaceutical carrier" is a pharmaceutically acceptable solvent, suspending agent or carrier for delivering a compound of Formula I, II to a subject. The carrier may be a liquid or a solid, which is selected according to the intended mode of administration. Each carrier must be pharmaceutically "acceptable" in terms of the compatibility with other ingredients of the composition and no harm to the subjects.

The compounds of formula I, II can be administered orally, topically or parenterally, in dosage unit formulations containing conventional non-toxic pharmaceutically acceptable carriers, adjuvants and excipients. The term "parenterally" as used herein includes subcutaneous injection for the administration of aerosols to the lungs or nasal cavity, intravenous, intramuscular, intrathecal, intracranial injection or infusion techniques.

The present invention also provides novel therapeutic methods for topical, oral and parenteral pharmaceutical formulations suitable for use in the present invention. The compounds of the present invention can be orally administered in the form of tablets, aqueous or oily suspensions, troches, lozenges, powders, granules, emulsions, capsules, syrups or elixirs. Compositions for oral use may contain one or more agents selected from the group consisting of sweeteners, flavoring agents, coloring agents, and preservatives to prepare pharmaceutically delicious formulations. Suitable sweeteners include sucrose, lactose, glucose, aspartame or saccharin. Suitable disintegrants include corn starch, methylcellulose, polyvinylpyrrolidone, xanthan gum, bentonite, alginic acid or agar. Suitable flavoring agents include peppermint oil, wintergreen oil, cherry, orange or raspberry flavoring. Suitable preservatives include sodium benzoate, vitamin E, α-tocopherol, ascorbic acid, methylparaben, propylparaben or sodium bisulfite. Suitable lubricants include magnesium stearate, stearic acid, sodium oleate, sodium chloride or talc. Suitable delay agents include glyceryl monostearate or glyceryl distearate. Tablets contain a mixture of active ingredients and non-toxic pharmaceutically acceptable excipients that are suitable for the preparation of a tablet.

These excipients may be, for example, (1) an inert diluents, such as calcium carbonate, lactose, calcium phosphate or sodium phosphate; (2) a granulating and disintegrating agent, such as corn starch or alginic acid; (3) a bonding agent, such as starch, gelatin or Arabic gum; (4) a lubricant, such as magnesium stearate, stearic acid or talc. These tablets may be uncoated or coated by the prior art to delay their disintegration and absorption in the gastrointestinal tract, thereby providing a sustained action over a longer period of time. For example, a delay material may be used, such as glyceryl monostearate or glyceryl distearate. Coating may also be carried out according to the techniques described in U.S. Pat. Nos. 4,522,587, 4,256,108, 4,160,452, and 4,265,874, to form osmotic therapeutic tablets for controlled release.

The compounds of formula I, II and the pharmaceutically active agents used herein may be administered alone or together for in vivo application, parenteral injection or gradual infusion. The route of administration can be intravenous, intraarterial, intraperitoneal, intramuscular, subcutaneous, intraluminal, transdermal or by infusion via, for example, an osmotic pump. For in vitro studies, reagents may be added or dissolved in a suitable biologically acceptable buffer and added to the cells or tissues.

Formulations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, alcohol/aqueous solution, emulsion or suspension, including saline and buffering media. Parenteral carriers include sodium chloride solution, Ringer's glucose, dextrose and sodium chloride, lactated Ringer's intravenous carriers include liquid and nutritional supplements, electrolyte supplements (e.g., based on Ringer's dextrose), etc. Preservatives and other additives may also be present, such as antimicrobials, antioxidants, chelating agents, growth factors and inert gases, etc.

The present invention includes various pharmaceutical compositions used for ameliorating diseases. A pharmaceutical composition according to one embodiment of the invention is prepared by a compound of formula I or II, an analog, derivative or salt thereof, or a combination of a compound of formula I or II with one or more pharmaceutically active agents. The carriers, excipients and additives or adjuvants are used to prepare the compositions in a form suitable for administration to subjects. Commonly used carriers or auxiliaries include magnesium carbonate, titanium dioxide, lactose, mannitol and other sugars, talc, milk proteins, gelatin, starch, vitamins, cellulose and its derivatives, animal and vegetable oils, polyethylene glycols and solvents, such as sterile water, alcohol, glycerin and polyols. Intravenous carriers include liquid and nutritional supplements. Preservatives include antimicrobials, antioxidants, chelating agents and inert gases. Other pharmaceutically acceptable carriers include aqueous solutions, non-toxic excipients, including salts, preservatives, buffers, etc.

The compounds of formula I or II may also be administered in the form of liposome delivery systems, such as small unilamellar vesicles, large unilamellar vesicles, and multilamellar vesicles. Liposomes can be formed by a variety of phospholipids, such as cholesterol, stearamide or phosphatidylcholine.

The compounds of formula I or II can also be used in the form of veterinary compositions which can be prepared, for example, by conventional methods in the art. Examples of such veterinary compositions include those suitable for:
(a) oral administration, external use, such as infusion (for example, aqueous or non-aqueous solutions or suspensions); tablets or bolus; powders, granules or particles for mixing with feeds; pastes suitable for tongues;
(b) parenteral administration, such as, by subcutaneous, intramuscular or intravenous injection, for example, as a sterile solution or suspension; or (where appropriate) by intramammary injection, wherein the milk suspension or solution is introduced into breasts via the nipples;
(c) topical application, for example, as a cream, ointment or spray applied to the skin; or
(d) endovaginal application, for example, as a pessary, cream or foam.

The term "therapeutically effective amount" refers to an amount of a compound of formula I or II of the present invention effective to produce the desired therapeutic response. A "prophylactically effective amount" has a similar definition.

The present invention is further illustrated by the following embodiments, but these embodiments are not intended to limit the scope of the invention. Tables 1-4 summarize the structures of representative compounds of the invention.

Embodiment 1

Preparation of Tricyclic Formamide with Hydroxyl Group

The preparation procedure: tricyclic carboxylic acid (III, A=OH) (1.1 g, 5.6 mmol) and DMF (10 mL), 3 molar equivalents of alcoholamine and O-benzotriazole-tetramethylurea hexafluorophosphate (HBTU, 2.55 g, 6.7 mmol) were added to a dry round-bottom flask. After magnetic stirring at room temperature for 10-20 minutes, N, N-diisopropylethylamine (1.44 g, 11.2 mmol) was slowly added, and then the reaction solution was heated to 50° C. for 12 hours, and the extent of reaction was tracked by TLC. After completion of the reaction, the mixture was cooled and the reaction solution was poured into ice water, extracted with ethyl acetate, and the extracting solutions were combined, and the solvent was evaporated under reduced pressure after drying. The residue was separated and purified by column chromatography using the eluent of ethyl acetate: petroleum ether at a ratio of 1:1-1:9. The eluent was concentrated and then recrystallized from a mixed solvent of ethyl acetate and petroleum ether to give an alcohol of the formula (VI).

Embodiment 2

Preparation of a Compound of the Formula (VII)

The alcohol of the formula (VI) (1 g), dichloromethane (10 ml) and 1.5 equivalents of triethylamine were added to a dry round-bottom flask. After magnetic stirring under ice-water cooling condition for 10-20 minutes, 1.3 molar equivalents of methylsulfonyl chloride was slowly added, and the reaction was carried out for 1 hour, and the extent of reaction was tracked by TLC. After completion of the reaction, 20 ml of an aqueous sodium hydrogencarbonate solution was added, and after stirring for 10 minutes, the layers were separated, and the aqueous layer was extracted with dichloromethane, and the extracting solutions were combined and washed with diluted hydrochloric acid, aqueous solution of sodium hydrogencarbonate, and aqueous solution of saturated sodium chloride respectively. After drying, the solvent was evaporated under reduced pressure to give a crude product of compound of formula (VII), and then purified by recrystallization from a mixed solvent of ethyl acetate and petroleum ether.

Embodiment 3

Amination of a Compound of Formula (VII)

The compound of the formula (VII) (0.1 g), DMSO (2 ml) and 3 molar equivalents of an amine of the formula (VIII) were added to a dry round-bottom flask. After stirring at room temperature overnight, 20 ml of water was added, and after stirring for 10 minutes, the mixture was extracted with dichloromethane, then the extracting solutions were combined and washed with diluted hydrochloric acid, aqueous solution of sodium hydrogencarbonate, and aqueous solution of saturated sodium chloride respectively. After drying, the solvent was evaporated under reduced pressure to give compounds of the formula (I) and formula (II).

Embodiment 4

Preparation of Acridine-4-carboxylic Acid

Acridine-4-carboxylic acid was prepared with reference to the method in (J. Med. Chem. 2003, 46, 183-189 and Bioorg. Med. Chem. Lett. 2014, 24, 5710-5715). $^1$H NMR (d$_6$-DMSO) δ 7.61-7.77 (m, 2H), 7.95-8.00 (m, 1H), 8.24-8.26 (m, 1H), 8.30-8.31 (m, 1H), 8.38 (d, 1H), 8.72-8.74 (m, 1H), 9.35 (d, 1H), 12.73 (br, 1H).

Embodiment 5

Preparation of N-(2-hydroxypropyl) Acridine-4-carboxamide

The procedure was the same as that described in Embodiment 1. The tricyclic acid was acridine-4-carboxylic acid prepared in Embodiment 4, and the alkanolamine was 2-hydroxypropylamine, the yield was 83%. $^1$H NMR (d$_6$-DMSO): δ 1.16 (d, J=6.9 Hz, 3H), 2.82 (br s, 1H), 3.52 (dd, J=11.0, 6.0 Hz, 1H), 5.10 (t, J=5.4 Hz, 1H), 7.63-8.42 (m, 6H), 8.75 (d, J=6.2 Hz, 1H, ArH-3), 9.35 (s, 1H, ArH-9), 11.85 (t, J=5.4 Hz, 1H, CONH).

Embodiment 6

Preparation of N-(2-methyl-2-methanesulfonyloxyethyl) Acridine-4-carboxamide

The procedure was the same as that described in Embodiment 2. The alcohol of the formula (VI) was N-(2-hydroxypropyl) acridine-4-carboxamide prepared in Embodiment 5, and the yield was 93%. $^1$H NMR (d$_6$-DMSO): δ 1.31 (d, J=6.9 Hz, 3H), 2.82 (br s, 1H), 3.52 (dd, J=11.0, 6.0 Hz, 1H), 4.50 (br s, 3H), 5.10 (t, J=5.4 Hz, 1H), 7.63-8.42 (m, 6H), 8.75 (d, J=6.2 Hz, 1H, ArH-3), 9.35 (s, 1H, ArH-9), 11.85 (t, J=5.4 Hz, 1H, CONH).

Embodiment 7

Compound N-[2-(N-isopropylmethylamino)propyl] acridine-4-carboxamide (10)

The procedure was the same as that described in Embodiment 3. The compound of the formula (VII) is N-(2-methanesulfonyloxypropyl) acridine-4-carboxamide prepared in Embodiment 6, and the amine of the formula (VIII) is N-isopropylmethylamine. The yield was 78%. $^1$H NMR (D$_2$O) δ 1.05 (d, J=7.2 Hz, 6H), 3.10 (m, 1H), 3.12 (s, 3H, NCH$_3$), 3.61 (m, 1H), 4.02 (dd, J=6.2 Hz, 2H, NHCH$_2$), 7.02 (m, 1H), 7.88 (m, 1H), 7.95 (m, 1H), 8.30 (m, 1H), 8.44-8.61 (m, 2H), 9.47 (s, 1H), 10.82 (t, J=5.4 Hz, 1H, CONH).

Embodiment 8

Preparation of N-(1-methyl-2-hydroxyethyl) Acridine-4-carboxamide

The procedure was the same as that described in Embodiment 1. The tricyclic acid was acridine-4-carboxylic acid, and the alkanolamine was 2-amino-1-propanol. The yield was 86%. $^1$H NMR (d$_6$-DMSO): δ 1.17 (d, J=6.9 Hz, 3H), 2.81 (br s, 1H), 3.53 (dd, J=11.0, 6.0 Hz, 1H), 5.10 (t, J=5.4 Hz, 1H), 7.63-8.42 (m, 6H), 8.75 (d, J=6.2 Hz, 1H, ArH-3), 9.35 (s, 1H, ArH-9), 11.23 (t, J=5.4 Hz, 1H, CONH).

Embodiment 9

Preparation of N-(1-methyl-2-methanesulfonyloxyethyl) Acridine-4-carboxamide

The procedure was the same as that described in Embodiment 2. The alcohol of the formula (VI) is N-(1-methyl-2-hydroxyethyl) acridine-4-carboxamide prepared in Embodiment 8. The yield was 88%. $^1$H NMR (d6-DMSO): δ 1.32 (d, J=6.9 Hz, 3H), 2.84 (br s, 1H), 3.51 (dd, J=11.0, 6.0 Hz, 1H), 4.51 (br s, 3H), 5.12 (t, J=5.4 Hz, 1H), 7.63-8.42 (m, 6H), 8.75 (d, Hz, 1H, ArH-3), 9.35 (s, 1H, ArH-9), 11.85 (t, J=5.4 Hz, 1H, CONH).

Embodiment 10

Compound N-[1-methyl-2-(N-isopropylmethylamino) ethyl] acridine-4-carboxamide (26)

The procedure was the same as that described in Embodiment 3. The compound of the formula (VII) was N-[1-methyl-2-(N-isopropylmethylamino) ethyl] acridine-4-carboxamide prepared in Embodiment 9, and the amine of the formula (VIII) was N-isopropylmethylamine. The yield was 77%. $^1$H NMR (D$_2$O) δ 1.05 (d, J=7.2 Hz, 6H), 3.10 (m, 1H), 3.12 (s, 3H, NCH$_3$), 3.61 (m, 1H), 4.02 (dd, J=6.2 Hz, 2H, NHCH$_2$), 7.02 (m, 1H), 7.88 (m, 1H), 7.95 (m, 1H), 8.30 (m, 1H), 8.44-8.61 (m, 2H), 9.47 (s, 1H), 11.33 (t, J=5.4 Hz, 1H, CONH).

Embodiment 11

Preparation of 1-methyl-9-carboxyphenazine 1-methyl-9-carboxyphenazine was prepared with reference to the methods in the literature (J. Med. Chem. 2000, 43, 1350-1358). mp 110-112° C. NMR $^1$H NMR (300 MHz, CDCl$_3$) δ 2.10 (s, 3H, CH$_3$), 7.72 (d, J=8.2 Hz, 1H, H-3), 8.03-8.11 (m, 2H, H-7, 8), 8.32 (dd, J=8.4, 1.8 Hz, 1H, H-6 or H-4), 8.49 (dd, J=7.6, 1.6 Hz, 1H, H-6 or H-4), 8.91 (d, J=7.7 Hz, 1H, H-2), 15.35 (s, 1H, CO$_2$H).

Embodiment 12

Preparation of N-(2-hydroxypropyl)-1-methylphenazine-9-carboxamide

The procedure was the same as that described in Embodiment 1. Tricyclic carboxylic acid was 1-methyl-9-carboxyphenazine, and the alkanolamine was 2-hydroxypropylamine. The yield was 83%. $^1$H NMR (300 MHz, CDCl$_3$) δ 1.15 (d, J=6.9 Hz, 31-1), 2.11 (s, 3H, CH$_3$), 2.82 (br s, 1H), 3.51 (dd, J=11.0, 6.0 Hz, 1H), 3.67 (dd, J=11.0, 3.8 Hz, 1H), 4.05 (m, 1H), 5.88 (br s, 1H), 7.72 (d, J=8.2 Hz, 1H, H-3), 8.03-8.11 (m, 2H, H-7, 8), 8.32 (dd, J=8.4, 1.8 Hz, 1H, H-6 or H-4), 8.49 (dd, J=7.6, 1.6 Hz, 1H, H-6 or H-4), 8.91 (d, J=7.7 Hz, 1H, H-2), 11.84 (t, J=5.4 Hz, 1H, CONH).

Embodiment 13

Preparation of N-(2-methanesulfonyloxypropyl)-1-methylphenazine-9-carboxamide

The procedure was the same as that described in Embodiment 2. The alcohol of the formula (VI) was N-(2-hydroxypropyl) 1-methylphenazine-9-carboxamide prepared in Embodiment 12. The yield was 90%. $^1$H NMR (300 MHz, CDCl$_3$) δ 1.13 (d, J=6.9 Hz, 3H), 2.12 (s, 3H, CH$_3$), 2.81 (br s, 1H), 3.52 (dd, J=11.0, 6.0 Hz, 1H), 3.64 (dd, J=11.0, 3.8 Hz, 1H), 4.05 (m, 1H), 4.51 (br s, 3H), 5.88 (br s, 1H), 7.72 (d, J=8.2 Hz, 1H, H-3), 8.03-8.11 (m, 2H, H-7, 8), 8.32 (dd, J=8.4, 1.8 Hz, 1H, H-6 or H-4), 8.49 (dd, J=7.6, 1.6 Hz, 1H, H-6 or H-4), 8.91 (d, J=7.7 Hz, 1H, H-2), 11.84 (t, J=5.4 Hz, 1H, CONH).

Embodiment 14

Preparation of N-[2-(N-isopropylmethylamino)propyl]-1-methylphenazine-9-carboxamide (50)

The procedure was the same as that described in Embodiment 3. The compound of the formula (VII) was N-(2-methanesulfonyloxypropyl)-1-methylphenazine-9-carboxamide prepared in Embodiment 13, and the amine of the formula (VIII) was N-isopropylmethylamine. The yield was 77%, $^1$H NMR (300 MHz, CDCl$_3$) δ 1.05 (d, J=7.2 Hz, 6H), 3.10 (m, 1H), 3.12 (s, 3H, NCH$_3$), 3.61 (m, 1H), 4.02 (dd, J=6.2 Hz, 2H, NHCH$_2$), 4.05 (m, 1H), 5.88 (br s, 1H), 7.72 (d, J=8.2 Hz, 1H, H-3), 8.03-8.11 (m, 2H, H-7, 8), 8.32 (dd, J=8.4, 1.8 Hz, 1H, H-6 or H-4), 8.49 (dd, J=7.6, 1.6 Hz, 1H, H-6 or H-4), 8.91 (d, J=7.7 Hz, 1H, H-2), 11.84 (t, J=5.4 Hz, 1H, CONH).

Embodiment 15

Preparation of N-(1-methyl-2-hydroxyethyl) 1-methylphenazine-9-carboxamide

The procedure was the same as that described in Embodiment 1. The tricyclic carboxylic acid was 1-methyl-9-carboxyphenazine, and the alkanolamine was 2-aminopropanol. The yield was 80%. $^1$H NMR (300 MHz, CDCl$_3$) δ 1.16 (d, J=6.9 Hz, 3H), 2.10 (s, 3H, CH$_3$), 2.82 (br s, 1H), 3.52 (dd, J=11.0, 6.0 Hz, 1H), 3.66 (dd, J=11.0, 3.8 Hz, 1H), 4.05 (m, 1H), 5.88 (br s, 1H), 7.72 (d, J=8.2 Hz, 1H, H-3), 8.03-8.11 (m, 2H, H-7, 8), 8.32 (dd, J=8.4, 1.8 Hz, 1H, H-6 or H-4), 8.49 (dd, J=7.6, 1.6 Hz, 1H, H-6 or H-4), 8.91 (d, J=7.7 Hz, 1H, H-2), 11.86 (t, J=5.4 Hz, 1H, CONH).

Embodiment 16

Preparation of N-(1-methyl-2-methanesulfonyloxyethyl-methylphenazine-9-carboxamide The procedure was the same as that described in Embodiment 2. The alcohol of the formula (VI) was N-(1-methyl-2-hydroxyethyl) 1-methylphenazine-9-carboxamide prepared in Embodiment 15. The yield was 90%. $^1$H NMR (300 MHz, CDCl$_3$) δ1.15 (d, J=6.9 Hz, 3H), 2.12 (s, 3H, CH$_3$), 2.83 (br s, 1H), 3.55 (dd, J=11.0, 6.0 Hz, 1H), 3.68 (dd, J=11.0, 3.8 Hz, 1H), 4.05 (m, 1H), 4.51 (br s, 3H), 5.88 (br s, 1H), 7.72 (d, J=8.2 Hz, 1H, H-3), 8.03-8.11 (m, 2H, H-7, 8), 8.32 (dd, J=8.4, 1.8 Hz, 1H, H-6 or H-4), 8.49 (dd, J=7.6, 1.6 Hz, 1H, H-6 or H-4), 8.91 (d, 7.7 Hz, 1H, H-2), 11.86 (t, J=5.4 Hz, 1H, CONH).

Embodiment 17

Preparation of N-[1-methyl-2-(N-isopropylmethylamino)ethyl]-1-methylphenazine-9-carboxamide (66)

The procedure was the same as that described in Embodiment 3. The compound of the formula (VII) was N-(1-methyl-2-methanesulfonyloxyethyl) 1-methylphenazine-9-carboxamide prepared in Embodiment 16, and the amine of the formula (VIII) was N-isopropylmethylamine. The yield was 76%. $^1$H NMR (300 MHz, CDCl$_3$) δ 1.06 (d, J=7.2 Hz, 6H), 3.11 (m, 1H), 3.12 (s, 3H, NCH$_3$), 3.61 (m, 1H), 4.02 (dd, J=6.2 Hz, 2H, NHCH$_2$), 5.88 (br s, 1H), 7.72 (d, J=8.2 Hz, 1H, H-3), 8.03-8.11 (m, 2H, H-7, 8), 8.32 (dd, J=8.4, 1.8 Hz, 1H, H-6 or H-4), 8.49 (dd, J=7.6, 1.6 Hz, 1H, H-6 or H-4), 8.91 (d, J=7.7 Hz, 1H, H-2), 11.86 (t, J=5.4 Hz, 1H, CONH).

Embodiment 18

Preparation of 2,6-dimethyl-1-oxo-1,2-dihydrobenzo[b][1,6]naphthyridine-4-carboxylic acid It was prepared according to the method in the patent (AU2003221640B2). $^1$H NMR (d$_6$-DMSO): δ 2.73 (s, 3H, CH$_3$), 3.76 (s, 3H, N—CH$_3$), 7.65 (t, 1H, J=7.6 Hz, H-8), 7.93 (d, 1H, J=6.6 Hz), 8.24 (d, 1H, J=8.1 Hz), 8.84 (s, 1H, H-3), 9.48 (s, 1H, H-10), 16.3 (s, 1H, COOH).

Embodiment 19

Preparation of N-(2-hydroxyethyl)-2,6-dimethyl-1-oxo-1,2-dihydrobenzo[b][1,6]naphthyridine-4-carboxamide The procedure was the same as that described in Embodiment 1. The tricyclic carboxylic acid was 2,6-dimethyl-1-oxo-1,2-dihydrobenzo [b][1,6]naphthyridine-4-carboxylic acid, and the alkanolamine was ethanolamine. The yield was 82%. $^1$H NMR (d$_6$-DMSO): δ 2.73 (s, 3H, CH$_3$), 3.63 (q, J=5.8 Hz, 2H, CH$_2$CH$_2$—OH), 3.73 (q, J=5.8 Hz, 2H, CH$_2$CH$_2$OH), 3.76 (s, 3H, N—CH$_3$), 5.10 (t, J=5.4 Hz, 1H, CH$_2$CH$_2$OH), 7.65 (t, 1H, J=7.6 Hz, H-8), 7.93 (d, 1H, J=6.6 Hz), 8.24 (d, 1H, J=8.1 Hz), 8.84 (s, 1H, H-3), 9.48 (s, 1H, H-10), 11.44 (t, J=5.4 Hz, 1H, CONH).

Embodiment 20

Preparation of N-(2-methanesulfonyloxyethyl)-2,6-dimethyl-1-oxo-1,2-dihydrobenzo[b][1,6]naphthyridine-4-carboxamide The procedure was the same as that described in Embodiment 2. The alcohol of the formula (VI) was N-(2-hydroxyethyl)-2,6-dimethyl-1-oxo-1,2-dihydrobenzo[b][1, 6]naphthyridine-4-carboxamide prepared in Embodiment 19. The yield was 89%. NMR (d$_6$-DMSO): δ 2.75 (s, 3H, CH$_3$), 3.64 (q, J=5.8 Hz, 2H, CH$_2$CH$_2$—OH), 3.72 (q, J=5.8 Hz, 2H, CH$_2$CH$_2$OMs), 3.74 (s, 3H, N—CH$_3$), 4.51 (br s, 3H), 5.11 (t, J=5.4 Hz, 1H, CH$_2$CH$_2$OH), 7.65 (t, 1H, J=7.6 Hz, H-8), 7.93 (d, 1H, J=6.6 Hz), 8.24 (d, 1H, J=8.1 Hz), 8.84 (s, 1H, H-3), 9.48 (s, 1H, H-10), 11.23 (t, J=5.4 Hz, 1H, CONH).

Embodiment 21

Preparation of N-[2-(N-isopropylmethylamino)ethyl]-2,6-dimethyl-1-oxo-1,2-dihydrobenzo[b][1, 6]naphthyridine-4-carboxamide (93)

The procedure was the same as that described in Embodiment 3. The compound of the formula (VII) is N-(2-methanesulfonyloxyethyl)-2,6-dimethyl-1-oxo-1,2-dihydrobenzo[b][1,6] naphthyridine-4-carboxamide prepared in Embodiment 20, and the amine of formula (VIII) was N-isopropylmethylamine. The yield was 69%. $^1$H NMR (d$_6$-DMSO): δ 1.06 (d, J=7.2 Hz, 6H), 2.75 (s, 3H, CH$_3$), 3.10 (m, 1H), 3.12 (s, 3H, NCH$_3$), 3.61 (m, 2H), 4.02 (dd, J=6.2 Hz, 2H, NHCH$_2$), 3.74 (s, 3H, N—CH$_3$), 7.65 (t, 1H, J=7.6 Hz, H-8), 7.93 (d, 1H, J=6.6 Hz), 8.24 (d, 1H, J=8.1 Hz), 8.84 (s, 1H, H-3), 9.48 (s, 1H, H-10), 11.23 (t, J=5.4 Hz, 1H, CONH).

Embodiment 22

Preparation of 2-(4-fluorophenyl)-6-methyl-1-oxo-1,2-dihydrobenzo[b][1,6]naphthyridine-4-carboxylic Acid It was prepared according to the method in the patent (AU2003221640B2). $^1$H NMR (d$_6$-DMSO): δ 2.74 (s, 3H), 7.38-7.45 (n, 1H), 7.60-7.43 (m, 1H), 7.61-7.71 (m, 1H), 7.95-7.96 (m, 1H), 8.25 (d, 2H), 8.48 (s, 1H), 9.53 (s, 1H).

Embodiment 23

Preparation of N-[(1-methylpyrrol-2-yl) methyl]-2-(4-fluorophenyl)-6-methyl-1-oxo-1,2-dihydrobenzo[b][1, 6]naphthyridine-4-carboxamide (108)

The procedure was the same as that described in Embodiment 1. The tricyclic acid was 2-(4-fluorophenyl)-6-methyl-1-oxo-1,2-dihydrobenzo [b][1,6]naphthyridine-4-carboxylic acid prepared in Embodiment 22 and the alkanolamine was replaced by 1-methyl-2-aminomethylpyrrolidine. The yield was 57%. $^1$H NMR (d$_6$-DMSO): δ 1.60 (m, 4H), 2.00 (s, 3H), 2.30 (m, 5H), 2.75 (s, 3H, CH$_3$), 3.10 (n, 4H), 3.54, m, 1H0, 3.61 (m, 2H), 4.02 (m, 2H), 3.63 (m, 2H), 3.73 (n, 2H), 6.15 (m, 1H), 7.38-7.43 (m, 2-H), 7.60-7.77 (m, 3H), 7.95 (d, J=6.0 Hz, 1H), 8.25 (d, J=8.4 Hz, 1H), 8.48 (s, 1H), 11.85 (t, J=5.4 Hz, 1H, CONH).

Embodiment 24

Preparation of N-(2-methyl-2-hydroxyethyl)-2,6-dimethyl-1-oxo-1,2-dihydrobenzo[b][1,6]naphthyridine-4-carboxamide The procedure was the same as that described in Embodiment 1. The tricyclic acid was 2,6-dimethyl-1-oxo-1,2-dihydrobenzo[b][1,6]naphthyridine-4-carboxylic acid, and the alkanolamine was 2-hydroxypropylamine. The yield was 79%. $^1$H NMR (d$_6$-DMSO): δ 1.14 (d, J=6.9 Hz, 3H), 2.74 (s, 3H, CH$_3$), 2.81 (br s, 1H), 3.53 (dd, J=11.0, 6.0 Hz, 1H), 3.65 (dd, =11.0, 3.8 Hz, 1H), 3.76 (s, 3H, N—CH$_3$), 4.05 (m, 1H), 5.88 (br s, 1H), 7.65 (t, 1H, J=7.6 Hz, H-8), 7.93 (d, 1H, J=6.6 Hz), 8.24 (d, 1H, J=8.1 Hz), 8.84 (s, 1H, H-3), 9.48 (s, 1H, H-10), 11.85 (t, J=5.4 Hz, 1H, CONH).

Embodiment 25

Preparation of N-(2-methyl-2-methanesulfonyloxyethyl)-2,6-dimethyl-1-oxo-1,2-dihydrobenzo[b][1,6]naphthyridine-4-carboxamide The procedure was the same as that described in Embodiment 2. The alcohol of the formula (VI) was N-(2-methyl-2-hydroxyethyl)-2,6-dimethyl-1-oxo-1,2-dihydrobenzoate [b][1,6]naphthyridine-4-carboxamide prepared in Embodiment 24. The yield was 86%. $^1$H NMR (d$_6$-DMSO): δ 1.15 (d, J=6.9 Hz, 3H), 2.75 (s, 3H, CH$_3$), 2.81 (br s, 1H), 3.51 (dd, =11.0, 6.0 Hz, 1H), 3.61 (dd, J=11.0, 3.8 Hz, 1H), 3.72 (s, 3H, N—CH$_3$), 4.05 (m, 1H), 4.51 (br s, 3H), 5.88 (br s, 1H), 7.65 (t, 1H, J=7.6 Hz, H-8), 7.93 (d, 1H, J=6.6 Hz), 8.24 (d, 1H, J=8.1 Hz), 8.84 (s, 1H, H-3), 9.48 (s, 1H, H-10), 11.85 (t, J=5.4 Hz, 1H, CONH).

Embodiment 26

Preparation of N-[2-methyl-2-(N-isopropylmethylamino)ethyl]-2,6-dimethyl-1-oxo-1,2-dihydrobenzo[b][1, 6]naphthyridine-4-carboxamide (114)

The procedure was the same as that described in Embodiment 3. The compound of the formula (VII) was N-(2-methyl-2-methanesulfonyloxyethyl)-2,6-dimethyl-1-oxo-1,2-dihydrobenzo[b][1,6]naphthyridine-4-carboxamide prepared in the Embodiment 25, and the amine of formula (VIII) was N-isopropylmethylamine. The yield was 59%. $^1$H NMR (d$_6$-DMSO): δ 1.06 (d, J=7.2 Hz, 6H), 3.11 (m, 1H), 3.12 (s, 3H, NCH$_3$), 3.61 (m, 1H), 3.72 (s, 3H, N—CH$_3$), 4.02 (dd, J=6.2 Hz, 2H, NHCH$_2$), 4.05 (m, 1H), 5.88 (br s, 1H), 7.65 (t, 1H, J=7.6 Hz, H-8), 7.93 (d, 1H, J=6.6 Hz), 8.24 (d, 1H, J=8.1 Hz), 8.84 (s, 1H, H-3), 9.48 (s, 1H, H-10), 11.00 (t, J=5.4 Hz, 1H, CONH).

Embodiment 27

Preparation of N-(1-methyl-2-hydroxyethyl)-2,6-dimethyl-1-oxo-1,2-dihydrobenzo[b][1,6]naphthyridine-4-carboxamide The procedure was the same as that described in Embodiment 1. The tricyclic acid was 2,6-dimethyl-1-oxo-1,2-dihydrobenzo[b][1,6]naphthyridine-4-carboxylic acid, and the alkanolamine was 2-aminopropanol. The yield was 82%. $^1$H NMR (d$_6$-DMSO): δ 1.16 (d, J=6.9 Hz, 3H), 2.73 (s, 3H, CH$_3$), 2.82 (br s, 1H), 3.52 (dd, J=11.0, 6.0 Hz, 1H), 3.66 (dd, J=11.0, 3.8 Hz, 1H), 3.76 (s, 3H, N—CH$_3$), 4.05 (m, 1H), 5.88 (br s, 1H), 7.65 (t, 1H, J=7.6 Hz, H-8), 7.93 (d, 1H, J=6.6 Hz), 8.24 (d, 1H, J=8.1 Hz), 8.84 (s, 1H, H-3), 9.48 (s, 1H, H-10), 11.85 (t, J=5.4 Hz, 1H, CONH).

Embodiment 28

Preparation of N-(1-methyl-2-methanesulfonyloxyethyl)-2,6-dimethyl-1-oxo-1,2-dihydrobenzo[b][1,6]naphthyridine-4-carboxamide The procedure was the same as that described in Embodiment 2. The alcohol of the formula (VI) was N-(1-methyl-2-hydroxyethyl)-2,6-dimethyl-1-oxo-1,2-dihydrobenzo[b][1,6]naphthyridine-4-carboxamide prepared in Embodiment 27. The yield was 81%. $^1$H NMR (d$_6$-DMSO): δ 1.13 (d, J=6.9 Hz, 3H), 2.71 (s, 3H, CH$_3$), 2.85 (br s, 1H), 3.22 (dd, J=11.0, 6.0 Hz, 1H), 3.36 (dd, J=11.0, 3.8 Hz, 1H), 3.76 (s, 3H, N—CH$_3$), 4.05 (m, 1H), 4.51 (br s, 3H), 5.88 (br s, 1H), 7.65 (t, 1H, J=7.6 Hz, H-8), 7.93 (d, 1H, J=6.6 Hz), 8.24 (d, 1H, J=8.1 Hz), 8.84 (s, 1H, H-3), 9.48 (s, 1H, H-10), 11.85 (t, J=5.4 Hz, 1H, CONH).

Embodiment 29

Preparation of N-[1-methyl-2-(N-isopropylmethylamino)ethyl]-2,6-dimethyl-1-oxo-1,2-dihydrobenzo[b][1,6]naphthyridine-4-carboxamide (130)

The procedure was the same as that described in Embodiment 3. The compound of the formula (VII) was N-(1-methyl-2-methanesulfonyloxyethyl)-2,6-dimethyl-1-oxo-1,2-dihydrobenzo[b][1,6]naphthyridine-4-carboxamide prepared in Embodiment 28, and the amine of formula (VIII) was N-isopropylmethylamine. The yield was 55%. $^1$H NMR (d$_6$-DMSO): δ 1.06 (d, J=7.2 Hz, 6H), 3.11 (m, 1H), 3.12 (s, 3H, NCH$_3$), 3.61 (m, 1H), 3.76 (s, 3H, N—CH$_3$), 4.02 (dd, J=6.2 Hz, 2H, NHCH$_2$), 4.05 (m, 1H), 5.88 (br s, 1H), 7.65 (t, 1H, J=7.6 Hz, H-8), 7.93 (d, 1H, J=6.6 Hz), 8.24 (d, 1H, J=8.1 Hz), 8.84 (s, 1H, H-3), 9.48 (s, 1H, H-10), 11.85 (t, J=5.4 Hz, 1H, CONH).

Embodiment 30

Preparation of 2-ethyl-6-methyl-1-oxo-1,2-dihydrobenzo[b][1,6]naphthyridine-4-carboxylic Acid It was prepared according to the method in the patent No. AU2003221640B2. $^1$H NMR (d$_6$-DMSO): δ 1.30 (t, J=7.1 Hz, 3H, CH$_2$CH$_3$), 2.65 (s, 3H, ArCH$_3$), 4.12 (q, J=7.1 Hz, 2H, CH$_2$CH$_3$), 7.59 (t, J=7.6 Hz, 1H, H-8), 7.86 (d, J=6.8 Hz, 1H, H-7), 8.12 (d, J=8.3 Hz, 1H, H-9), 8.74 (s, 1H, H-3), 9.36 (s, 1H, H-10), 15.89 (s, 1H, COOH).

Embodiment 31

Preparation of N-(2-hydroxyethyl)-2-ethyl-6-methyl-1-oxo-1,2-dihydrobenzo[b][1,6]naphthyridine-4-carboxamide The procedure was the same as that described in Embodiment 1. The tricyclic acid was 2-ethyl-6-methyl-1-oxo-1,2-dihydrobenzo[b][1,6]naphthyridine-4-carboxylic acid, and the alkanolamine was ethanolamine. The yield was 75%. $^1$H NMR (d$_6$-DMSO): δ 1.30 (t, J=7.1 Hz, 3H, CH$_2$CH$_3$), 2.65 (s, 3H, ArCH$_3$), 3.63 (q, J=5.8 Hz, 2H, CH$_2$CH$_2$—OH), 3.73 (q, J=5.8 Hz, 2H, CH$_2$CH$_2$OH), 4.12 (q, J=7.1 Hz, 2H, CH$_2$CH$_3$), 5.10 (t, J=5.4 Hz, 1H, CH$_2$CH$_2$OH), 7.59 (t, J=7.6 Hz, 1H, H-8), 7.86 (d, J=6.8 Hz, 1H, H-7), 8.12 (d, J=8.3 Hz, 1H, H-9), 8.74 (s, 1H, H-3), 9.36 (s, 1H, H-10), 11.85 (t, J=5.4 Hz, 1H, CONH).

Embodiment 32

Preparation of N-(2-methanesulfonyloxyethyl)-2-ethyl-6-methyl-1-oxo-1,2-dihydrobenzo[b][1,6]naphthyridine-4-carboxamide The procedure was the same as that described in Embodiment 2. The alcohol of the formula (VI) was N-(2-hydroxyethyl)-2-ethyl-6-methyl-1-oxo-1,2-dihydrobenzo[b][1,6]naphthyridine-4-carboxamide prepared in Embodiment 31. The yield was 75%. $^1$H NMR (d$_6$-DMSO): δ 1.31 (t, J=7.1 Hz, 3H, CH$_2$CH$_3$), 2.65 (s, 3H, ArCH$_3$), 3.41 (m, 2H), 3.53 (m, 2H), 4.12 (q, J=7.1 Hz, 2H, CH$_2$CH$_3$), 4.51 (br s, 3H), 7.59 (t, J=7.6 Hz, 1H, H-8), 7.86 (d, J=6.8 Hz, 1H, H-7), 8.12 (d, J=8.3 Hz, 1H, H-9), 8.74 (s, 1H, H-3), 9.36 (s, 1H, H-10), 11.85 (t, J=5.4 Hz, 1H, CONH).

Embodiment 33

Preparation of N-[2-(N-ethylmethylamino)ethyl]-2-ethyl-6-methyl-1-oxo-1,2-dihydrobenzo[b][1,6]naphthyridine-4-carboxamide (90)

The procedure was the same as that described in Embodiment 3. The compound was N-(2-methanesulfonyloxyethyl)-2-ethyl-6-methyl-1-oxo-1,2-dihydrobenzo[b][1,6]naphthyridine-4-carboxamide prepared in Embodiment 32, and the amine of the formula (VIII) was N-ethylmethylamine. The yield was 83%, $^1$H NMR (d$_6$-DMSO): δ 1.06 (d, J=7.2 Hz, 3H), 2.75 (s, 3H, CH$_3$), 3.10 (m, 2H), 3.12 (s, 3H, NCH$_3$), 3.61 (m, 2H), 4.02 (dd, J=6.2 Hz, 2H, NHCH$_2$), 4.12 (q, J=7.1 Hz, 2H, CH$_2$CH$_3$), 7.59 (t, J=7.6 Hz, 1H, H-8), 7.86 (d, J=6.8 Hz, 1H, H-7), 8.12 (d, J=8.3 Hz, 1H, H-9), 8.74 (s, 1H, H-3), 9.36 (s, 1H, H-10), 11.85 (t, J=5.4 Hz, 1H, CONH).

Embodiment 34

Preparation of N-(2-hydroxypropyl)-2-ethyl-6-methyl-1-oxo-1,2-dihydrobenzo[b][1,6]naphthyridine-4-carboxamide The procedure was the same as that described in Embodiment 1. The tricyclic acid was 2-ethyl-6-methyl-1-oxo-1,2-dihydrobenzo[b][1,6]naphthyridine-4-carboxylic acid, and the alkanolamine was 2-hydroxypropylamine. The yield was 70%. $^1$H NMR (d$_6$-DMSO): δ 1.14 (d, J=6.9 Hz, 3H), 1.30 (t, J=7.1 Hz, 3H, CH$_2$CH$_3$), 2.65 (s, 3H, ArCH$_3$), 2.81 (br s, 1H), 3.53 (dd, J=11.0, 6.0 Hz, 1H), 3.65 (dd, J=11.0, 3.8 Hz, 1H), 3.76 (s, 3H, N—CH$_3$), 4.05 (m, 1H), 4.12 (q, J=7.1 Hz, 2H, CH$_2$CH$_3$), 7.59 (t, J=7.6 Hz, 1H, H-8), 7.86 (d, J=6.8 Hz, 1H, H-7), 8.12 (d, J=8.3 Hz, 1H, H-9), 8.74 (s, 1H, H-3), 9.36 (s, 1H, H-10), 11.85 (t, J=5.4 Hz, 1H, CONH).

Embodiment 35

Preparation of N-(2-methanesulfonyloxypropyl)-2-ethyl-6-methyl-1-oxo-1,2-dihydrobenzo [b][1,6] naphthyridine-4-carboxamide The procedure was the same as that described in Embodiment 2. The alcohol of the formula (VI) was N-(2-hydroxypropyl)-2-ethyl-6-methyl-1-oxo-1,2-dihydrobenzo [b][1, 6]naphthyridine-4-carboxamide prepared in Embodiment 34. The yield was 77%. $^1$H NMR (d$_6$-DMSO): δ 1.12 (d, J=6.9 Hz, 3H), 1.31 (t, J=7.1 Hz, 3H, CH$_2$CH$_3$), 2.65 (s, 3H, ArCH$_3$), 2.81 (br s, 1H), 3.23 (dd, J=11.0, 6.0 Hz, 1H), 3.65 (dd, J=11.0, 3.8 Hz, 1H), 3.76 (s, 31-1, N—CH$_3$), 4.51 (br s, 3H), 4.12 (q, J=7.1 Hz, 2H, CH$_2$CH$_3$), 7.59 (t, J=7.6 Hz, 1H, H-8), 7.86 (d, J=6.8 Hz, 1H, H-7), 8.12 (d, J=8.3 Hz, 1H, H-9), 9.36 (s, 1H, H-3), 9.36 (s, 1H, H-10), 11.85 (t, J=5.4 Hz, 1H, CONH).

Embodiment 36

Preparation of N-[2-methyl-2-(N-isopropylethylamino)ethyl]-2-ethyl-6-methyl-1-oxo-1,2-dihydrobenzo[b][1, 6]naphthyridine-4-carboxamide (115)

The procedure was the same as that described in Embodiment 3. The compound of the formula (VII) was N-(2-methanesulfonyloxypropyl)-2-ethyl-6-methyl-1-oxo-1,2-dihydrobenzo[b][1, 6]naphthyridine-4-carboxamide prepared in Embodiment 35, and the amine of formula (VIII) was N-isopropylethylamine. The yield was 60%, $^1$H NMR (d$_6$-DMSO): δ 1.05 (d, J=7.2 Hz, 6H), 3.10 (m, 2H), 1.12 (d, J=6.9 Hz, 3H), 1.31 (t, J=7.1 Hz, 3H, CH$_2$CH$_3$), 1.35 (t, J=7.1 Hz, 3H, CH$_2$CH$_3$), 2.65 (s, 3H, ArCH$_3$), 2.81 (br s, 1H), 3.12 3.61 (m, 1H), 3.23 (dd, J=11.0, 6.0 Hz, 1H), 3.65 (dd, J=11.0, 3.8 Hz, 1H), 3.76 (s, 3H, N—CH$_3$), 4.02 (dd, J=6.2 Hz, 2H, NHCH$_2$), 4.12 (q, J=7.1 Hz, 2H, CH$_2$CH$_3$), 7.59 (t, J=7.6 Hz, 1H, H-8), 7.86 (d, J=6.8 Hz, 1H, H-7), 8.12 (d, J=8.3 Hz, 1H, H-9), 8.74 (s, 1H, H-3), 9.36 (s, 1H, H-10), 11.85 (t, J=5.4 Hz, 1H, CONH).

Embodiment 37

Preparation of N-(1-methyl-2-hydroxyethyl)-2-ethyl-6-methyl-1-oxo-1,2-dihydrobenzo[b][1,6] naphthyridine-4-carboxamide The procedure was the same as that described in Embodiment 1. The tricyclic acid was 2-ethyl-6-methyl-1-oxo-1,2-dihydrobenzo[b][1,6]naphthyridine-4-carboxylic acid, and the alkanolamine was 2-aminopropanol. The yield was 80%. $^1$H NMR (d$_6$-DMSO): δ 1.13 (d, J=6.9 Hz, 3H), 1.31 (t, J=7.1 Hz, 3H, CH$_2$CH$_3$), 2.66 (s, 3H, ArCH$_3$), 2.82 (br s, 1H), 3:53 (dd, J=11.0, 6.0 Hz, 1H), 3.65 (dd, J=11.0, 3.8 Hz, 1H), 3.76 (s, 3H, N—CH$_3$), 4.05 (m, 1H), 4.12 (q, J=7.1 Hz, 2H, CH$_2$CH$_3$), 7.59 (t, J=7.6 Hz, 1H, H-8), 7.86 (d, J=6.8 Hz, 1H, H-7), 8.12 (d, J=8.3 Hz, 1H, H-9), 8.74 (s, 1H, H-3), 9.36 (s, 1H, H-10), 11.85 (t, J=5.4 Hz, 1H, CONH).

Embodiment 38

Preparation of N-(1-methyl-2-methanesulfonyloxyethyl)-2-ethyl-6-methyl-1-oxo-1,2-dihydrobenzo[b] [1,6]naphthyridine-4-carboxamide The procedure was the same as that described in Embodiment 2. The alcohol of the formula (VI) was N-(1-methyl-2-hydroxyethyl)-2-ethyl-6-methyl-1-oxo-1,2-dihydrobenzo [b][1, 6]naphthyridine-4-carboxamide prepared in Embodiment 37. The yield was 82%, $^1$H NMR (d$_6$-DMSO): δ 1.12 (d, J=6.9 Hz, 3H), 1.33 (t, J=7.1 Hz, 3H, CH$_2$CH$_3$), 2.65 (s, 3H, ArCH$_3$), 2.81 (br s, 1H), 3.23 (dd, J=11.0, 6.0 Hz, 1H), 3.65 (dd, J=11.0, 3.8 Hz, 1H), 3.76 (s, 3H, N—CH$_3$), 4.51 (br s, 3H), 4.12 (q, J=7.1 Hz, 2H, CH$_2$CH$_3$), 7.59 (t, J=7.6 Hz, 1H, H-8), 7.86 (d, J=6.8 Hz, 1H, H-7), 8.12 (d, J=8.3 Hz, 1H, H-9), 8.74 (s, 1H, H-3), 9.36 (s, 1H, H-10), 11.85 (t, J=5.4 Hz, 1H, CONH).

Embodiment 39

Preparation of N-[1-methyl-2-(N-isopropylethylamino)ethyl]-2-ethyl-6-methyl-1-oxo-1,2-dihydrobenzo[b][1,6]naphthyridine-4-carboxamide (131)

The procedure was the same as that described in Embodiment 3. The compound of the formula (VII) was N-(1-methyl-2-methanesulfonyloxyethyl)-2-ethyl-6-methyl-1-oxo-1,2-dihydrobenzo[b][1, 6]naphthyridine-4-carboxamide prepared in Embodiment 38, and the amine of formula (VIII) was N-isopropylethylamine. The yield was 60%, NMR (d$_6$-DMSO): δ 1.05 (d, J=7.2 Hz, 6H), 3.10 (m, 2H), 1.12 (d, J=6.9 Hz, 3H), 1.31 (t, J=7.1 Hz, 3H, CH$_2$CH$_3$), 1.35 (t, J=7.1 Hz, 3H, CH$_2$CH$_3$), 2.65 (s, 3H, ArCH$_3$), 2.81 (br s, 1H), 3.12 (m, 1H), 3.23 (dd, J=11.0, 6.0 Hz, 1H), 3.65 (dd, J=11.0, 3.8 Hz, 1H), 3.76 (s, 3H, N—CH$_3$), 4.02 (dd, J=6.2 Hz, 2H, NHCH$_2$), 4.12 (q, J=7.1 Hz, 2H, CH$_2$CH$_3$), 7.59 (t, J=7.6 Hz, 1H, H-8), 7.86 (d, J=6.8 Hz, 1H, H-7), 8.12 (d, J=8.3 Hz, 1H, H-9), 8.74 (s, 1H, H-3), 9.36 (s, 1H, H-10), 11.85 (t, J=5.4 Hz, 1H, CONH).

Embodiment 40

Preparation of N-(2-hydroxyethyl)-2-(4-fluorophenyl)-6-methyl-1-oxo-1,2-dihydrobenzo[b][1,6]naphthyridine-4-carboxamide The procedure was the same as that described in Embodiment 1. The tricyclic acid was 2-(4-fluorophenyl)-6-methyl-1-oxo-1,2-dihydrobenzo[b][1,6]naphthyridine-4-carboxylic acid prepared in Embodiment 22 and the alkanolamine was ethanolamine. The yield was 80%, $^1$H NMR (d$_6$-DMSO): δ 2.75 (s, 3H, CH$_3$), 3.63 (q, J=5.8 Hz, 2H, CH$_2$CH$_2$—OH), 3.73 (q, J=5.8 Hz, 2H, CH$_2$CH$_2$OH), 5.10 (t, J=5.4 Hz, 1H, CH$_2$CH$_2$OH), 7.38-7.43 (m, 2-H), 7.60-7.77 (m, 3H), 7.95 (d, J=6.0 Hz, 1H), 8.25 (d, J=8.4 Hz, 1H), 8.48 (s, 1H), 11.85 (t, J=5.4 Hz, 1H, CONH).

Embodiment 41

Preparation of N-(2-methanesulfonyloxyethyl)-2-(4-fluorophenyl)-6-methyl-1-oxo-1,2-dihydrobenzo[b] [1,6]naphthyridine-4-carboxamide The procedure was the same as that described in Embodiment 2. The alcohol of the formula (VI) was N-(2-hydroxyethyl)-2-(4-fluorophenyl)-6-methyl-1-oxo-1,2-dihydrobenzo[b][1, 6]naphthyridine-4-carboxamide prepared in Embodiment 40. The yield was 80%. $^1$H NMR (d$_6$-DMSO): δ 2.75 (s, 3H, CH$_3$), 3.63 (q, J=5.8 Hz, 2H, CH$_2$CH$_2$OH), 3.73 (q, J=5.8 Hz, 2H, CH$_2$CH$_2$OH), 4.51 (br s, 3H), 7.38-7.43 (m, 2-H), 7.60-7.77 (m, 3H), 7.95 (d, J=6.0 Hz, 1H), 8.25 (d, J=8.4 Hz, 1H), 8.48 (s, 1H), 11.85 (t, J=5.4 Hz, 1H, CONH).

Embodiment 42

Preparation of N-[2-(N, N-diethylamino) ethyl]-2-(4-fluorophenyl)-6-methyl-1-oxo-1,2-dihydrobenzo[b][1, 6]naphthyridine-4-carboxamide (91)

The procedure was the same as that described in Embodiment 3. The compound of the formula (VII) was N-(2-methanesulfonyloxyethyl)-2-(4-fluorophenyl)-6-methyl-1-oxo-1,2-dihydrobenzo[b][1, 6]naphthyridine-4-carboxamide prepared in Embodiment 41, and the amine of the formula (VIII) was diethylamine. The yield was 67%. $^1$H NMR (d$_6$-DMSO): δ 1.06 (m, 6H), 2.75 (s, 3H, CH$_3$), 3.10 (m, 4H), 3.61 (m, 2H), 4.02 (m, 2H), 3.63 (m, 2H), 3.73 (m, 2H), 7.38-7.43 (m, 2-H), 7.60-7.77 (m, 3H), 7.95 (d, J=6.0 Hz, 1H), 8.25 (d, J=8.4 Hz, 1H), 8.48 (s, 1H), 11.85 (t, J=5.4 Hz, 1H, CONH).

Embodiment 43

Preparation of N-(2-hydroxypropyl)-2-(4-fluorophenyl)-6-methyl-1-oxo-1,2-dihydrobenzo[b][1,6]naphthyridine-4-carboxamide The procedure was the same as that described in Embodiment 1. The tricyclic acid was 2-(4-fluorophenyl)-6-methyl-1-oxo-1,2-dihydrobenzo[b][1, 6]naphthyridine-4-carboxylic acid, and the alkanolamine was 2-hydroxypropylamine. The yield was 81%. $^1$H NMR (d$_6$-DMSO): δ 1.16 (d, J=6.9 Hz, 3H), 2.75 (s, 3H, CH$_3$), 2.82 (br s, 1H), 3.52 (dd, J=11.0, 6.0 Hz, 1H), 3.66 (dd, J=11.0, 3.8 Hz, 1H), 4.05 (m, 1H), 7.38-7.43 (m, 2-H), 7.60-7.77 (m, 3H), 7.95 (d, J=6.0 Hz, 1H), 8.25 (d, J=8.4 Hz, 1H), 8.48 (s, 1H), 11.85 (t, J=5.4 Hz, 1H, CONH).

Embodiment 44

Preparation of N-(2-methanesulfonyloxypropyl)-2-(4-fluorophenyl)-6-methyl-1-oxo-1,2-dihydrobenzo[b][1,6]naphthyridine-4-carboxamide The procedure was the same as that described in Embodiment 2. The alcohol of the formula (VI) was N-(2-hydroxypropyl)-2-(4-fluorophenyl)-6-methyl-1-oxo-1,2-dihydrobenzo[b][1, 6]naphthyridine-4-carboxamide prepared in Embodiment 43. The yield was 85%. $^1$H NMR (d$_6$-DMSO): δ 1.15 (d, J=6.9 Hz, 3H), 2.77 (s, 3H, CH$_3$), 2.81 (br s, 1H), 3.52 (m, 1H), 3.66 (m, 1H), 4.05 (m, 1H), 4.51 (br s, 3H), 7.38-7.43 (m, 2-H), 7.60-7.77 (m, 3H), 7.95 (d, J=6.0 Hz, 1H), 8.25 (d, J=8.4 Hz, 1H), 8.48 (s, 1H), 11.85 (t, J=5.4 Hz, 1H, CONH).

Embodiment 45

Preparation of N-[2-methyl-2-(N-isobutylmethylamino)ethyl]-2-(4-fluorophenyl)-6-methyl-1-oxo-1,2-dihydrobenzo[b][1, 6]naphthyridine-4-carboxamide (121)

The procedure was the same as that described in Embodiment 3. The compound of the formula (VII) was N-(2-methanesulfonyloxypropyl)-2-(4-fluorophenyl)-6-methyl-1-oxo-1,2-dihydrobenzo[b][1, 6]naphthyridine-4-carboxamide prepared in Embodiment 44, and the amine of formula (VIII) is N-isobutylmethylamine. The yield was 55%. $^1$H NMR (d$_6$-DMSO): δ 1.05 (d, J=7.2 Hz, 6H), 1.08 (m, 1H), 3.10 (m, 2H), 1.15 (d, J=6.9 Hz, 3H), 2.77 (s, 3H, CH$_3$), 2.81 (br s, 1H), 3.12 (s, 3H, NCH$_3$), 3.61 (m, 1H), 4.02 (dd, J=6.2 Hz, 2H, NHCH$_2$), 3.52 (m, 1H), 3.66 (m, 1H), 4.05 (m, 1H), 7.38-7.43 (m, 2-H), 7.60-7.77 (m, 3H), 7.95 (d, J=6.0 Hz, 1H), 8.25 (d, J=8.4 Hz, 1H), 8.48 (s, 1H), 11.85 (t, J=5.4 Hz, 1H, CONH).

Embodiment 46

Preparation of N-(1-methyl-2-hydroxyethyl)-2-(4-fluorophenyl)-6-methyl-1-oxo-1,2-dihydrobenzo[b][1, 6]naphthyridine-4-carboxamide The procedure was the same as that described in Embodiment 1. The tricyclic acid was 2-(4-fluorophenyl)-6-methyl-1-oxo-1,2-dihydrobenzo[b][1, 6]naphthyridine-4-carboxylic acid, and the alkanolamine was 2-aminopropanol. The yield was 80%. $^1$H NMR (d$_6$-DMSO): δ 1.15 (d, J=6.9 Hz, 3H), 2.76 (s, 3H, CH$_3$), 2.81 (br s, 1H), 3.52 (dd, J=11.0, 6.0 Hz, 1H), 3.65 (dd, J=11.0, 3.8 Hz, 1H), 4.05 (m, 1H), 7.38-7.43 (m, 2-H), 7.60-7.77 (m, 3H), 7.95 (d, J=6.0 Hz, 1H), 8.25 (d, J=8.4 Hz, 1H), 8.48 (s, 1H), 11.85 (t, J=5.4 Hz, 1H, CONH).

Embodiment 47

Preparation of N-(1-methyl-2-methanesulfonyloxyethyl)-2-(4-fluorophenyl)-6-methyl-1-oxo-1,2-dihydrobenzo[b][1, 6]naphthyridine-4-carboxamide The procedure was the same as that described in Embodiment 2. The alcohol of the formula (VI) was N-(1-methyl-2-hydroxyethyl)-2-(4-fluorophenyl)-6-methyl-1-oxo-1,2-dihydrobenzo[b][1, 6]naphthyridine-4-carboxamide prepared in Embodiment 46. The yield was 80%. $^1$H NMR (d$_6$-DMSO): δ 1.23 (d, J=6.9 Hz, 3H), 2.74 (s, 3H, CH$_3$), 2.81 (br s, 1H), 3.51 (m, 1H), 3.65 (m, 1H), 4.05 (m, 1H), 4.51 (br s, 3H), 7.38-7.43 (m, 2-H), 7.60-7.77 (m, 3H), 7.95 (d, J=6.0 Hz, 1H), 8.25 (d, J=8.4 Hz, 1H), 8.48 (s, 1H), 11.85 (t, J=5.4 Hz, 1H, CONH).

Embodiment 48

Preparation of N-[2-methyl-2-(N-cyclopropylmethylamino)ethyl]-2-(4-fluorophenyl)-6-methyl-1-oxo-1,2-dihydrobenzo[b][1, 6]naphthyridine-4-carboxamide (133)

The procedure was the same as that described in Embodiment 3. The compound of the formula (VII) was N-(1-methyl-2-methanesulfonyloxyethyl)-2-(4-fluorophenyl)-6-methyl-1-oxo-1,2-dihydrobenzo[b][1, 6]naphthyridine-4-carboxamide prepared in Embodiment 47, and the amine of the formula (VIII) was N-cyclopropylmethylamine. The yield was 50%, $^1$H NMR (d$_6$-DMSO): δ 1.13 (m, 4H), 1.23 (d, J=6.9 Hz, 3H), 2.74 (s, 3H, CH$_3$), 2.81 (br s, 1H), 3.10 (m, 1H), 3.51 (m, 1H), 3.65 (m, 1H), 4.05 (m, 1H), 7.38-7.43 (m, 2-H), 7.60-7.77 (m, 3H), 7.95 (d, J=6.0 Hz, 1H), 8.25 (d, J=8.4 Hz, 1H), 8.48 (s, 1H), 11.85 (t, J=5.4 Hz, 1H, CONH).

Embodiment 49

Preparation of 2,2'-{1,3-propanediyl bis [(methylimino)-2,1 ethanediyl]} bis{6-methyl-1-oxo-1,2-dihydrobenzo[b][ 1, 6]naphthyridine-4-carboxylic acid}

It was prepared according to the method in the patent No. AU2003221640B2. $^1$H NMR (d$_6$-DMSO): δ 1.45-1.49 (m, 2H), 2.13 (s, 6H, 2×N—CH3), 2.28-2.34 (m, 4H), 2.48-2.55 (m, 10H), 4.01-4.05 (m, 4H), 7.36 (t, J=7.4 Hz, 2H), 7.62 (d, J=6.5 Hz, 2H), 7.93 (d, J=7.7 Hz, 2H), 8.49 (s, 2H), 9.13 (s, 2H).

Embodiment 50

Preparation of 2,2'-{1,3-propanediyl bis[(methylimino)-2,1 ethanediyl]} bis{N-(2-hydroxyethyl)-6-methyl-1-oxo-1,2-dihydrobenzo [b][1,6]naphthyridin-4-carboxamide}

The procedure was the same as that described in Embodiment 1. The tricyclic acid was 2,2'-{1,3-propanediyl bis[(methylimino)-2,1 ethanediyl]} bis{6-methyl-1-oxo-1,2-dihydrobenzo[b][ 1, 6]naphthyridine-4-carboxylic acid}, and the alkanolamine was ethanolamine. The yield was 84%. $^1$H NMR (d$_6$-DMSO): δ 1.45-1.49 (m, 2H), 2.13 (s, 6H, 2×N—CH3), 2.28-2.34 (m, 4H), 2.48-2.55 (m, 10H), 3.63 (q, J=5.8 Hz, 4H, CH$_2$CH$_2$—OH), 3.73 (q, J=5.8 Hz, 4H, CH$_2$CH$_2$OH), 4.01-4.05 (m, 4H), 5.10 (t, J=5.4 Hz, 2H, CH$_2$CH$_2$OH), 7.36 (t, J=7.4 Hz, 2H), 7.62 (d, J=6.5 Hz, 2H), 7.93 (d, J=7.7 Hz, 2H), 8.49 (s, 2H), 11.85 (t, J=5.4 Hz, 2H, CONH).

Embodiment 51

Preparation of 2,2'-{1,3-propanediyl bis[(methylimino)-2,1 ethanediyl]} bis {N-(2-methanesulfonyloxyethyl)-6-methyl-1-oxo-1,2-dihydrobenzo[b][1, 6]naphthyridin-4-carboxamide}

The procedure was the same as that described in Embodiment 2. The alcohol was 2,2'-{1,3-propanediylbis[(methylimino)-2,1 ethanediyl]} bis{N-(2-hydroxyethyl)-6-methyl-1-oxo-1,2-dihydrobenzo[b][1, 6]naphthyridin-4-carboxamide}. The yield was 67%. $^1$H NMR (d$_6$-DMSO): δ 1.45-1.49 (m, 2H), 2.13 (s, 6H, 2×N—CH3), 2.28-2.34 (m, 4H), 2.48-2.55 (m, 10H), 3.63 (q, J=5.8 Hz, 4H, CH$_2$CH$_2$—OH), 3.73 (q, J=5.8 Hz, 4H, CH$_2$CH$_2$OH), 4.01-4.05 (m, 4H), 4.51 (br s, 6H), 7.36 (t, J=7.4 Hz, 2H), 7.62 (d, J=6.5 Hz, 2H), 7.93 (d, J=7.7 Hz, 2H), 8.49 (s, 2H), 11.85 (t, J=5.4 Hz, 2H, CONH).

Embodiment 52

Preparation of 2,2'-{1,3-propanediyl bis[(methylimino)-2,1 ethanediyl]} bis {N-[2-(N, N-diethylamino)ethyl]-6-methyl-1-oxo-1,2-dihydrobenzo[b] [1,6] naphthyridin-4-carboxamide} (134)

The procedure was the same as that described in Embodiment 3. 2,2'{1,3-propanediyl bis[(methylimino)-2,1 ethanediyl]} bis {N-(2-methanesulfonyloxyethyl)-6-methyl-1-oxo-1,2-dihydrobenzo[b][1, 6]naphthyridin-4-carboxamide} was reacted with diethylamine. The yield was 57%. $^1$H NMR (d$_6$-DMSO): δ 1.06 (m, 12H), 1.45-1.49 (m, 2H), 2.13 (s, 6H, 2×N—CH3), 2.28-2.34 (m, 4H), 2.48-2.55 (m, 10H), 2.75 (s, 6H, CH$_3$), 3.10 (m, 4H), 3.61 (m, 2H), 4.02 (m, 2H), 4.01-4.05 (m, 4H), 7.36 (t, J=7.4 Hz, 2H), 7.62 (d, J=6.5 Hz, 2H), 7.93 (d, J=7.7 Hz, 2H), 8.49 (s, 2H), 11.85 (t, J=5.4 Hz, 2H, CONH).

Embodiment 53

Preparation of 2,2'{1,3-propanediyl bis[(methylimino)-2,1 ethanediyl]} bis{N-(1-methyl-2-hydroxyethyl)-6-methyl-1-oxo-1,2-dihydrobenzo[b][1, 6]naphthyridin-4-carboxamide}

The procedure was the same as that described in Embodiment 1. The tricyclic acid was 2,2'-{1,3-propanediyl bis [(methylimino)-2,1 ethanediyl]} bis{6-methyl-1-oxo-1,2-dihydrobenzo[b][1, 6]naphthyridine-4-carboxylic acid}, and the alkanolamine was 2-aminopropanol. The yield was 83%. $^1$H NMR (d$_6$-DMSO): δ 1.16 (d, J=6.9 Hz, 6H), 1.45-1.49 (m, 2H), 2.13 (s, 6H, 2×N—CH3), 2.28-2.34 (m, 4H), 2.48-2.55 (m, 10H), 2.82 (br s, 2H), 3.52 (dd, J=11.0, 6.0 Hz, 2H), 3.66 (dd, J=11.0, 3.8 Hz, 2H), 4.01-4.05 (m, 6H), 5.88 (br s, 2H), 7.36 (t, J=7.4 Hz, 2H), 7.62 (d, J=6.5 Hz, 2H), 7.93 (d, J=7.7 Hz, 2H), 8.49 (s, 2H), 11.85 (t, J=5.4 Hz, 2H, CONH).

Embodiment 54

Preparation of 2,2'-{1,3-propanediyl bis[(methylimino)-2,1 ethanediyl]} bis {N-(1-methyl-2-methanesulfonyloxyethyl)-6-methyl-1-oxo-1,2-dihydrobenzo[b][1, 6]naphthyridin-4-carboxamide}

The procedure was the same as that described in Embodiment 2. 2,2'-{1,3-propanediyl bis[(methylimino)-2,1 ethanediyl]} bis {N-(1-methyl-2-hydroxyethyl)-6-methyl-1-oxo-1,2-dihydrobenzo[b][1, 6]naphthyridin-4-carboxamide} was used as the starting material. The yield was 89%. $^1$H NMR (d$_6$-DMSO): δ 1.15 (d, J=6.9 Hz, 6H), 1.45-1.49 (m, 2H), 2.13 (s, 6H, 2×N—CH3), 2.28-2.34 (m, 4H), 2.48-2.55 (m, 10H), 2.82 (br s, 2H), 3.52 (dd, J=11.0, 6.0 Hz, 2H), 3.66 (dd, J=11.0, 3.8 Hz, 2H), 4.01-4.05 (m, 6H), 4.51 (br s, 6H), 7.36 (t, J=7.4 Hz, 2H), 7.62 (d, J=6.5 Hz, 2H), 7.93 (d, J=7.7 Hz, 2H), 8.49 (s, 2H), 11.85 (t, J=5.4 Hz, 2H, CONH).

Embodiment 55

Preparation of 2,2'-{1,3-propanediylbis[(methylimino)-2,1 ethanediyl]} bis {N-[1-(N, N-diethylamino)ethyl])-6-methyl-1-oxo-1,2-dihydrobenzo [b][1, 6]naphthyridin-4-carboxamide} (139)

The procedure was the same as that described in Embodiment 3. 2,2'-{1,3-propanediyl bis[(methylimino)-2,1 ethanediyl]} bis{N-(1-methyl-2-methanesulfonyloxyethyl)-6-methyl-1-oxo-1,2-dihydrobenzo[b][1, 6]naphthyridin-4-carboxamide} was reacted with diethylamine. The yield was 57%, $^1$H NMR (d$_6$-DMSO): δ 1.06 (m, 12H), 1.15 (d, J=6.9 Hz, 6H), 1.45-1.49 (m, 2H), 2.13 (s, 6H, 2×N—CH3), 2.28-2.34 (m, 4H), 2.48-2.55 (m, 10H), 2.75 (s, 6H, CH$_3$), 2.82 (br s, 2H), 3.10 (m, 8H), 3.52 (dd, J=11.0, 6.0 Hz, 2H), 3.61 (m, 4H), 3.66 (dd, J=11.0, 3.8 Hz, 2H), 4.01-4.05 (m, 10H), 7.36 (t, J=7.4 Hz, 2H), 7.62 (d, J=6.5 Hz, 2H), 7.93 (d, J=7.7 Hz, 2H), 8.49 (s, 2H), 11.85 (t, J=5.4 Hz, 2H, CONH).

Embodiment 56

Preparation of 2,2'-{1,3-propanediyl bis[(methylimino)-2,1 ethanediyl]} bis{N-(2-hydroxypropyl)-6-methyl-1-oxo-1,2-dihydrobenzo[b][1, 6]naphthyridin-4-carboxamide}

The procedure was the same as that described in Embodiment 1. The tricyclic acid was 2,2'-{1,3-propanediyl bis[(methylimino)-2,1 ethanediyl]} bis {6-methyl-1-oxo-1,2-dihydrobenzo[b][1, 6]naphthyridine-4-carboxylic acid}, and the alkanolamine was 2-hydroxypropylamine. The yield was 78%. $^1$H NMR (d$_6$-DMSO): δ 1.17 (d, J=6.9 Hz, 6H), 1.45-1.49 (m, 2H), 2.13 (s, 6H, 2×N—CH3), 2.28-2.34 (m, 4H), 2.48-2.55 (m, 10H), 2.82 (br s, 2H), 3.52 (dd, J=11.0, 6.0 Hz, 2H), 3.66 (dd, J=11.0, 3.8 Hz, 2H), 4.01-4.05 (m, 6H), 5.88 (br s, 2H), 7.36 (t, J=7.4 Hz, 2H), 7.62 (d, J=6.5 Hz, 2H), 7.93 (d, J=7.7 Hz, 2H), 8.49 (s, 2H), 11.85 (t, J=5.4 Hz, 2H, CONH).

Embodiment 57

Preparation of 2,2'-{1,3-propanediylbis[(methylimino)-2,1 ethanediyl]} bis {N-(2-methyl-2-methanesulfonyloxyethyl)-6-methyl-1-oxo-1,2-dihydrobenzo[b][1, 6]naphthyridin-4-carboxamide)}

The procedure was the same as that described in Embodiment 2. The alcohol was 2,2'-{1,3-propanediyl bis[(methylimino)-2,1 ethanediyl]} bis{N-(2-hydroxypropyl)-6-methyl-1-oxo-1,2-dihydrobenzo[b][1, 6]naphthyridin-4-carboxamide}prepared in Embodiment 56. The yield was 80%. $^1$H NMR (d$_6$-DMSO): δ 1.14 (d, J=6.9 Hz, 6H), 1.45-1.49 (m, 2H), 2.13 (s, 6H, 2×N—CH3), 2.28-2.34 (m, 4H), 2.48-2.55 (m, 10H), 2.82 (br s, 2H), 3.52 (dd, J=11.0, 6.0 Hz, 2H), 3.66 (dd, J=11.0, 3.8 Hz, 2H), 4.01-4.05 (m, 6H), 4.51 (br s, 6H), 7.36 (t, J=7.4 Hz, 2H), 7.62 (d, J=6.5 Hz, 2H), 7.93 (d, J=7.7 Hz, 2H), 8.49 (s, 2H), 11.85 (t, J=5.4 Hz, 2H, CONH).

Embodiment 58

Preparation of 2,2'-{1,3-propanediylbis[(methylimino)-2,1 ethanediyl]} bis {N-[2-(N,N-diethylamino)ethyl])-6-methyl-1-oxo-1,2-dihydrobenzo[b][1, 6]naphthyridin-4-carboxamide} (144)

The procedure was the same as that described in Embodiment 3. The compound prepared in Embodiment 57 was used as a starting material to react with diethylamine. The yield was 58%. $^1$H NMR (d$_6$-DMSO): δ 1.04-1.08 (m, 12H), 1.15 (d, J=6.9 Hz, 6H), 1.45-1.49 (m, 2H), 2.13 (s, 6H, 2×N—CH3), 2.28-2.34 (m, 4H), 2.48-2.55 (m, 10H), 2.75 (s, 6H, CH$_3$), 2.82 (br s, 2H), 3.10 (m, 8H), 3.52 (dd, J=11.0, 6.0 Hz, 2H), 3.61 (m, 4H), 3.66 (dd, J=11.0, 3.8 Hz, 2H), 4.01-4.05 (m, 10H), 7.36 (t, J=7.4 Hz, 2H), 7.62 (d, J=6.5 Hz, 2H), 7.93 (d, J=7.7 Hz, 2H), 8.49 (s, 2H), 11.85 (t, J=5.4 Hz, 2H, CONH).

The synthesis of other compounds could be carried out with reference to the methods described above.

Embodiment 59

Biological Assay of the Compounds of the Invention

The in vitro cytotoxicity of the compounds of the present invention was tested with reference to the experimental methods reported in the literature (Liu Yanqin et al., Organic Chemistry, 2002, 22(4), 279-282). The human oral epithelial cancer cells (KB), human lung cancer cells (A-549), and breast cancer cells (MDA) were used to test the in vitro growth inhibition rate of the compounds by MTT assay. Cells were cultured at 37° C. for 3 days under a test drug concentration of 4 μg/mL. The results were summarized in Table 5.

TABLE 5

| Compound No. | KB | A549 | MDA |
| --- | --- | --- | --- |
| 5 | 1.5 | −11 | −5.1 |
| 6 | −5.0 | −5 | −1.5 |
| 7 | 2.2 | −5.8 | 4.4 |
| 8 | −4.5 | −6.6 | −4.7 |
| 10 | 5.3 | 3.3 | 1.2 |
| 22 | 1.2 | 3.1 | 2.5 |
| 44 | 6.1 | 7 | 6 |
| 47 | 5.1 | 6.7 | 9.0 |
| 48 | 6.5 | 3.9 | 4.6 |
| 50 | −5 | −7.8 | −7.2 |
| 66 | 0.9 | 1.2 | 1.9 |
| 85 | −7 | −3.4 | −1.8 |
| 86 | 7.6 | 9.8 | 14 |
| 87 | 4.4 | 5 | 3.9 |
| 88 | 2.8 | 1.6 | 1.4 |
| 90 | 4.5 | 3.5 | 6.4 |
| DACA (1) | 1.5 | 1.7 | 2.0 |

The results in Table 5 showed that the compounds of the invention had cytotoxic activity against animal and human tumor cell lines. Therefore, they have potential applications as anticancer drugs.

Those skilled in the art will appreciate that many variations and/or modifications can be made to the invention as shown in the specific embodiments without departing from the spirit and scope of the invention. Accordingly, the embodiments of the present invention are considered as illustrative and not restrictive in all aspects.

What is claimed is:

1. A tricyclic derivative compound, having a structural formula (I),

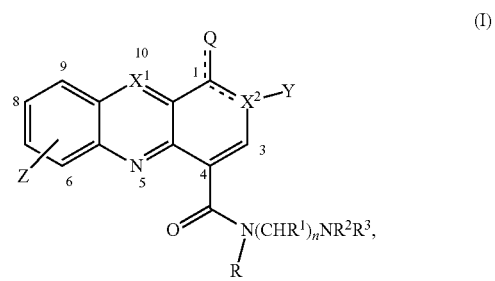

a position number in the formula is shown above, wherein
X$^1$ and X$^2$ may be —CH= or —N= respectively or simultaneously,
Q is O or S,
R and R$^1$-R$^3$ are independently H or optionally substituted C$_{1-4}$ alkyl or R and R$^1$-R$^3$ together with bonded nitrogen atoms to form an optionally substituted saturated or unsaturated heterocyclic group,
n is an integer from 0 to 6,
when X$^2$ is carbon, each R$^1$ is not H simultaneously; and when X$^2$ is nitrogen and n=2, R$^2$ and R$^3$ are not methyl simultaneously, Z is H, halogen, OH, $CO_2H$, $CO_2R^4$, $SO_2R^4$, $NR^4R^5$, nitro, cyano, $C_{1-6}$ alkyl, $C_{1-6}$ haloalkyl, $C_{1-6}$ alkoxy, $C_{1-6}$ haloalkoxy, $C_{1-6}$ aminoalkyl, $C_{1-6}$ aminoalkoxy, or aza functional group-substituted cyclic CH functional group, or bridged carbon or carbon/nitrogen skeleton at positions 6-7, 7-8 or 8-9, to form additional condensed 5- to 6-membered carbocyclic ring or heterocyclic ring, Y is H, $C_{1-6}$ alkyl, C1-6 haloalkyl, C1-6 alkoxy, C1-6 haloalkoxy, C1-6 aminoalkyl, C1-6 aminoalkoxy, or aza functional group-substituted cyclic CH functional group, or bridged carbon or carbon/nitrogen skeleton at positions 6-7, 7-8 or 8-9, to form additional condensed 5- to 6-membered carbocyclic ring or 15 heterocyclic ring, or $(CH_2)_m-X^2-(CH_2)_pU$, wherein $X^2$ is $CH_2$, C=O, CH=CH, O, S, NR, m and p are integers from 0 to 6, U is H, $CF_3$, halogen, $NR^4R^5$, $^+NRR^4R^5$, cyano, C(=O) $NR^4R^5$ $OR^4$, or $CO_2R^4$, optional substituents for $R^4$ and $R^5$ are the same as those defined for R and $R^1$-$R^3$, or a pharmaceutically acceptable salt, an N-oxide, a hydrate, a solvate, a pharmaceutically acceptable derivative, a tautomer and/or a stereoisomer of the compound, wherein, the compound is N-[2-(N-isopropylmethylamino)ethyl]-2,6-dimethyl-1-oxo-1,2-dihydrobenzo[b][1,6] naphthyridine-4-carboxamide.

* * * * *